(12) United States Patent
Schmidt et al.

(10) Patent No.: US 10,088,443 B2
(45) Date of Patent: Oct. 2, 2018

(54) CARRIER MATERIAL FOR ELECTRICALLY POLARIZABLE BIOMATERIALS, POLYELECTROLYTE MATERIALS, ATOMS, IONS AND MOLECULES; ITS MANUFACTURE AND USE

(75) Inventors: Heidemarie Schmidt, Dresden (DE); Christine Baumgart, Dresden (DE); Ilona Skorupa, Dresden (DE); Manfred Helm, Dresden (DE); Oliver G. Schmidt, Dresden (DE); Martin Müller, Dresden (DE)

(73) Assignees: HELMHOLTZ-ZENTRUM DRESDEN-ROSSENDORF E.V., Dresden (DE); LEIBNIZ-INSTITUT FÜR POLYMERFORSCHUNG DRESDEN E.V., Dresden (DE)

( * ) Notice: Subject to any disclaimer, the term of this patent is extended or adjusted under 35 U.S.C. 154(b) by 935 days.

(21) Appl. No.: 14/342,094

(22) PCT Filed: Aug. 31, 2012

(86) PCT No.: PCT/DE2012/200058
§ 371 (c)(1),
(2), (4) Date: Jun. 18, 2014

(87) PCT Pub. No.: WO2013/029609
PCT Pub. Date: Mar. 7, 2013

(65) Prior Publication Data
US 2014/0291143 A1    Oct. 2, 2014

(30) Foreign Application Priority Data

Aug. 31, 2011  (DE) .................. 10 2011 053 174
Nov. 7, 2011   (DE) .................. 10 2011 055 115
Jul. 16, 2012  (DE) .................. 10 2012 106 365

(51) Int. Cl.
*G01N 27/26* (2006.01)
*G01N 27/28* (2006.01)
(Continued)

(52) U.S. Cl.
CPC .......... *G01N 27/28* (2013.01); *G01N 27/327* (2013.01); *G01N 33/54366* (2013.01); *B01L 3/502761* (2013.01)

(58) Field of Classification Search
CPC ............ G01N 27/28; G01N 33/54366; G01N 27/327; B01L 3/502761
See application file for complete search history.

(56) References Cited

U.S. PATENT DOCUMENTS

| 4,255,505 A | 3/1981 | Hanada et al. |
| 6,538,298 B1 | 3/2003 | Weingarten et al. |

(Continued)

FOREIGN PATENT DOCUMENTS

| DE | 20 55 269 A1 | 5/1971 |
| DE | 103 44 915 A1 | 4/2005 |

(Continued)

OTHER PUBLICATIONS

R. R. Netz, J. F. Joanny, Macromolecules, 32, 9013 (1999).
(Continued)

*Primary Examiner* — Dennis White
(74) *Attorney, Agent, or Firm* — McGlew and Tuttle, P.C.

(57) ABSTRACT

Carriers for biomaterials, for polyelectrolyte materials, for electrically polarizable atoms, ions, molecules are provided wherein the material of the carriers is compatible with materials that are used in microelectronics. The arrangement of the biomaterials or biomolecules and optionally of biomolecules, biomaterials, biological functional units or (Continued)

cells adsorbed thereon can be affected with the carrier in a specific manner. Complex molecular machines can be built and tested by the carriers.

20 Claims, 12 Drawing Sheets

(51) Int. Cl.
G01N 27/327 (2006.01)
G01N 33/543 (2006.01)
B01L 3/00 (2006.01)

(56) References Cited

U.S. PATENT DOCUMENTS

| | | | |
|---|---|---|---|
| 7,687,111 B2 | 3/2010 | Lehmann | |
| 2002/0137059 A1* | 9/2002 | Wu | B01J 19/0046 435/6.19 |
| 2002/0149019 A1 | 10/2002 | Iwashita et al. | |
| 2003/0211637 A1 | 11/2003 | Schoeniger et al. | |
| 2004/0011650 A1 | 1/2004 | Zenhausern et al. | |
| 2008/0058229 A1 | 3/2008 | Berkland et al. | |
| 2008/0319247 A1 | 12/2008 | Forbes et al. | |

FOREIGN PATENT DOCUMENTS

| | | |
|---|---|---|
| DE | 10 2004 063 030 A1 | 8/2006 |
| EP | 0 645 811 B1 | 1/2000 |
| EP | 1 843 157 A1 | 10/2007 |
| EP | 2 198 953 A1 | 6/2010 |
| WO | 98/01758 A1 | 1/1998 |
| WO | 00/73777 A1 | 12/2000 |
| WO | 2005/007387 A1 | 1/2005 |
| WO | 2010 066432 A2 | 6/2010 |

OTHER PUBLICATIONS

A. V. Dobrynin, M. Rubinstein, Prog. Polym. Sci., 30, 1049-1118 (2005).
D. F. Williams: Definitions in Biomaterials. Progress in Biomedical Engineering, 4th ed. Elsevier, Amsterdam 1987.
M. Schmidt (vol. Ed.): Polyelectrolytes with Defined Molecular Architecture I, Springer, 2004, http://books.google.com/books?hl=en&lr=&id=YtFkEWo7kT4C&oi=fnd&pg=PR13&dq=M.+Schmidt+%28Vol.+Ed.%29:+Polyelectrolytes+with+Defined+Molecular+Architecture+1,+Springer,+2004&ots=_NNJwfN0uJ&sig=jKOoOKkeQSnzeQ5ARz7IDh4isYg#v=onepage&q&f=false.
Fleer et al., Polymers at Interfaces, Chapman, 1993, R. R. Netz, J. F. Joanny, Macromolecules, 32, 9013 (1999), A. V. Dobrynin, M. Rubinstein, Prog. Polym. Sci., 30, 1049-1118 (2005).
M. Müller, Orientation of α -helical Poly(L-lysine) in Consecutively Adsorbed Polyelectrolyte Multilayers on Texturized Silicon Substrates, Biomacromolecules, 2 (1), 262-269 (2001).
M. Müller, T. Reihs, W. Quyang, Needle like and spherical polyelectrolyte complex nanoparticles of poly(L-lysine) and copolymers of maleic acid, Langmuir, 21 (1), 465-469 (2005).
N. Balke et al.: Nanoscale mapping of ion diffusion in a lithium-ion battery cathode. Nature Nanotechnology 5 (2010), 749-754.
Pei Yu Chiou et al.: Massively parallel manipulation of single cells and microparticles using optical images. Nature 436 (2005) 370-372.
Goodsell, David S.: Wirtschaft and Produktion in der molekularen Welt [Economy and Production in the Molecular World], Translated by Hummel, Isolde, 2nd ed., 2010. Spektrum Akademischer Verlag.

M. E. Msall et al.: Ballistic phonon production in photoexcited Ge, GaAs, and Si. Phys. Rev. B. 65 (2002), 195205-1-7.
Javier Vicario et al.: Controlling the speed of rotation in molecular motors. Dramatic acceleration of the rotary motion by structural modification, Chem. Commun. (2005), 5910-5912.
B. Wang et al: Chemically Tunable Nanoscale Propellers of Liquids. Phys. Rev. Lett., 98 (2007), 266102-1-4.
Jean-Pierre Desvergne et al.: Cation complexing photochromic materials involving bisanthracenes linked by a polyether chain. Preparation of a crown-ether by photocycloisomerization; J. Chem. Soc., Chem. Commun. (1978), 403-404.
Jonathan E. Green et al.: A 160-kilobit molecular electronic memory patterned at 1011 bits per square centimeter. Nature, 445 (2007), 414-417.
Nesterov Alexander et al., "Precise selective deposition of microparticles on electrodes of microelectronic chips", Review of Scientific Instruments, AIP, Melville, NY, US, vol. 79, No. 3, Mar. 24, 2008, pp. 35106-35106.
K. König et al: "Programmable high voltage CMOS chips for particle-based high-density combinatorial peptide synthesis", Sensors and Actuators B: Chemical, vol. 147, No. 2, Jun. 3, 2010, pp. 418-427.
Ronald Pethig: "Dielectrophoresis: Status of the theory, technology, and applications", Biomicrofluidics, vol. 4, No. 2, Jan. 1, 2010, p. 022811.
Voldman Joel, "Electrical forces for microscale cell manipulation", Annual Review of Biomedical Engineering, vol. 8, 2006, pp. 425-454.
Wang X-B and Cheng J Ed—Cheng et al, "Electronic manipulation of cells on microchip-based devices", Jan. 1, 2001, Biochip Technology, Amsterdam : Harwood Academic Publ, pp. 135-139.
Manaresi N et al., "A CMOS chip for individual cell manipulation and detection", Solid-State Circuits Conference, 2003, Digest of Technical Papers. ISS CC. 2003 IEEE International San Francisco, CA, USA Feb. 9-13, 2003, Piscataway, NJ, USA, IEEE, US, Feb. 9, 2003, pp. 1-10.
Fuchs A B et al., "Electronic sorting and recovery of single live cells from microlite sized samples", Lab on a Chip, Royal Society of Chemistry, vol. 6, Jan. 1, 2006, pp. 121-126.
Gastrock G et al, "Sampling and monitoring in bioprocessing using microtechniques.", Journal of Biotechnology Dec. 2001, vol. 82, No. 2, Dec. 2001, pp. 123-135.
Primachenko et al., Electron states at the Si-SiO2 boundary, Semiconductor Physics, Quantum Electronics & Optoelectronics, 2005, V. 8, N 4, pp. 38-54.
Peterström et al., Si-SiO2 interface trap density in boron- and phosphorus-implanted silicon, APL, 63 (5), 1993, 672-674.
Thanh et al.,Elimination and Generation of Si-SiO2 Interface Traps by Low Temperature Hydrogen Annealing, J. Electrochem. Soc., 1988, 1797-1801.
Lee C et al., Sol-gel derived PNNZT thin films for micromachined piezoelectric force sensors, Thin Solid Films, Elsevier-Sequoia S.A. Lausanne, CH, Bd. 299, Nr. 1-2, May 15, 1997, pp. 88-93.
Aykutlu Dāna and Yoshihisa Yamamoto, Electrostatic force spectroscopy of near surface localized states, published Feb. 3, 2005, IOP Publishing Ltd, Nanotechnology, vol. 16, No. 3.
S. Sivasankar, S. Subramaniam, and D. Leckband, Direct molecular level measurements of the electrostatic properties of a protein surface, Proc. Natl. Acad. Sci. USA, vol. 95, pp. 12961-12966, Oct. 1998, Biophysics.
Shaohua Xu* and Morton F. Arnsdorf, Electrostatic force microscope for probing surface charges in aqueous solutions, Proc. Natl. Acad. Sci. USA, vol. 92, pp. 10384-10388, Oct. 1995, Biophysics.

* cited by examiner

CARRIER MATERIAL FOR ELECTRICALLY POLARIZABLE BIOMATERIALS, POLYELECTROLYTE MATERIALS, ATOMS, IONS AND MOLECULES; ITS MANUFACTURE AND USE

CROSS REFERENCE TO RELATED APPLICATIONS

This application is a United States National Phase Application of International Application PCT/DE2012/200058 filed Aug. 31, 2012 and claims the benefit of priority under 35 U.S.C. § 119 of German Patent Applications DE 10 2011 053 174.2 filed Aug. 31, 2011, DE 10 2011 055 115.8 filed Nov. 7, 2011 and DE 10 2012 106 365.6 filed Jul. 16, 2012, the entire contents of which are incorporated herein by reference.

FIELD OF THE INVENTION

The invention pertains to carrier materials (carriers) for electrically polarizable biomaterials, for structured single-component polyelectrolyte layers, multicomponent polyelectrolyte multilayers or layers of preformed polyelectrolyte complexes, for atoms, ions and/or molecules (epAIMP), to the manufacture and to the embodiment variants of these carriers for the manipulation, modification and motion of individual epAIMP up to the construction of molecular machines mM.

Manipulation of epAIMP is defined in the sense of the present invention as the attracting (binding), repulsion and sorting of epAIMP to the carrier.

Modification of epAIMP is defined in the sense of the present invention as the modification of individual chemical and/or physical properties of the epAIMP on the carrier.

Motion of epAIMP is defined in the sense of the present invention as the specifically directed motion of the epAIMP on or close to the surface of the carrier.

BACKGROUND OF THE INVENTION

Electrically polarizable biomaterials, structured, single-component polyelectrolyte layers, multicomponent polyelectrolyte multilayers or layers of preformed polyelectrolyte complexes, atoms, ions and/or molecules (epAIMP) are oriented in an electric field. A torque, which directs the dipole in the direction of the electric field, acts on the electric dipole of the epAIMP in a homogeneous electric field. In the inhomogeneous electric field, the dipole of the epAIMP is subject to a force, which pulls it into areas of higher field intensity.

The dynamics of the acting forces determines whether the forces of inertia, which counteract the motion of epAIMP in a homogeneous or inhomogeneous electric field, can be overcome. A recommended solution is the stick and slip method, i.e., the action of a slowly moving force in the desired direction and fast switch-off of the moving force.

A biomaterial is defined as a substance of natural or artificial origin that treats, improves or replaces any tissue, organ or any function of the body temporarily or permanently independently or as part of a whole (D. F. Williams: Definitions in Biomaterials. Progress in Biomedical Engineering, 4th ed. Elsevier, Amsterdam 1987).

Biomolecules are molecules of organic substances, which occur in living organisms. Biomolecules interact with biomaterials and define the biological environment for biomaterials. Biomolecules are defined in the sense of the present invention as all natural and artificial materials that occur in living organisms or are formed by living organisms, that are manufactured artificially and simulate natural, organic substances, or to which other (artificial) substances or metals can be added or have been added and/or which have formed connections with other artificial or natural materials.

Biomolecules may carry electrostatic charges and form an electric dipole. Such biomolecules are included among the epAIMP. The dipole-dipole interactions of the polar biomolecules ensure the orientation of the biomolecules among one another. On the nanometer length scale, the electrostatic interaction belongs to the forces with the greatest strength and also to those with the greatest range. Electrostatic forces are also very strong in aqueous solutions and thus keep the biomolecules away from each other.

In the study of biomaterials or biomolecules, the carrier must take up the biomaterials in a manner limitable in space and time and make the biomaterials available for local requirements. The adhesion to cells (adhesiveness to cells) of biomaterials and biomolecules on the carrier as well as cell mobility play an important role here. The underlying mechanisms of adhesion to cells or cell mobility have not been fully researched.

Distinction is made between biodegradable and non-biodegradable carriers for biomaterials.

Biomolecules may be hydrophobic or hydrophilic. Hydrophobic biomolecules are nonpolar. Hydrophilic biomolecules are polar and can be charged either positively (basic) or negatively (acidic).

The inverted optical or confocal microscope makes it possible to quantify the individual cell-cell and cell-surface interactions under physiological conditions. A plurality of important parameters of cellular adhesion, for example, maximum cell adhesion force, individual unfolding events, the tether characteristic as well as the total energy of the electrostatic bond can thus be determined.

To make it possible to carry out investigations on individual molecules by means of fluorescence detection on biomolecules under nearly physiological conditions, the biomolecules must have high fluorescence activity. Since very few molecules are intrinsically fluorescent or their fluorescence properties do not meet the requirements, biologically functional molecules are marked, as a rule, via covalent binding of stains developed specifically for this purpose (Sauer, Han et al., 1993).

Biomolecules with odd electrons have a magnetic moment that is stronger than the moment of a proton by about three orders of magnitude. This moment can be used as a probe in highly sensitive measurements with methods of electron spin resonance spectroscopy (EPR) in order to obtain information on a scale ranging from the atomic to the nanometer scale.

To construct biosensors, the biologically active elements must be fixed on carriers. Various methods are available for fixing, and distinction is made between physical and chemical methods. The physical methods include primarily adsorption. It is the simplest method. However, biosensors prepared in this manner respond sensitively to changes in the ambient conditions because of the reversible nature of the binding equilibrium. The chemical methods include covalent coupling and crosslinking Only the groups of the biomolecules that are not responsible for the biological activity may be involved in the covalent coupling with derivatized, water-insoluble carriers.

WO/2005/007387 A describes the nanomanipulation of the piezoelectric carrier by applying an electric voltage, which leads to a change in the contact area defined between carrier and biomaterial or biomolecule. The drawback is that these piezoelectric carriers must be thin so that the electric voltages applied do not become too high.

Despite the enormous technological advances made in the past years, there are only a small number of biosensory approaches with which a pharma screening can be carried out. The reasons for this are that the "classic" biosensor on the basis of enzymes and antibodies yields mostly only structural rather than functional information and the biomolecular interaction analysis with biosensors is very demanding. However, pharma screening can be given fresh impetus by microtechnologies and nanotechnologies by means of biosensors. In particular, the "High Content Screening" (HCS), a simultaneous screening of many effects, with biosensors appears to be feasible and could represent a way out of the currently developing bottlenecks in the development pipelines of many pharmaceutical companies.

Biosensors were developed in the past years for many different analytical tasks. Applications in the clinical medical area, fermentation control, quality control of foods and environmental analyses were in the foreground. However, the possibilities of using biosensory techniques are far more varied. On the one hand, highly specific structural elements, which are characteristic of potential drugs, can be recognized with biosensors; on the other hand, it is possible to carry out assays with which drug effects can then be detected. A biosensor typically comprises a biological recognition element and a physical sensor (transducer). Biosensors are usually classified according to the principle of function of their signal converter. Distinction is made essentially between electrochemical, optical, calorimetric and microgravimetric biosensors. However, such a classification is not meaningful in case of complex systems that contain whole living cells.

Polyelectrolyte materials have local electric dipoles, i.e., optionally positively or negatively charged functional groups, and can be bound with the forces or charge centers of the carriers acting as oppositely charged forces or charge centers by attractive electrostatic interaction (physisorption, adsorption). Such polyelectrolyte materials are included among the epAIMP.

Polyelectrolyte materials (PEL) [M. Schmidt (Vol. Ed.): Polyelectrolytes with Defined Molecular Architecture I, Springer, 2004] comprise single-component polyelectrolyte systems (PEE), whose charges have only one sign or which contain only one type of polyelectrolyte (e.g., negatively charged polyacrylic acid), as well as mixed polyelectrolyte systems, e.g., polyelectrolyte multilayers (PEM) or preformed polyelectrolyte complex particles (PEC). The different polyelectrolyte materials are shown schematically in FIG. 1.

Single-component PEL systems (PEE) are formed by simple adsorption from solutions of the respective PEL at a suitable concentration on the carriers. Mostly only inhomogeneous PEL layers (islands) are formed now in case of conventional substrates (lower surface charge density than those described here) because of the electrostatic self-repulsion between surface regions with already adsorbed PEL layers and the rest of the PEL in solution. The carriers in question here possess substantially higher surface charge densities (for values, see below). As a result, single-component PEL layers with substantially higher degree of occupation exceeding that in a monolayer can be formed or lead to adsorbed quantities of PEL that differ markedly from those that have hitherto been measured experimentally on highly charged substrates. As a result, new data can possibly be gained on the theory of the adsorption of polyelectrolytes on solid surfaces [e.g., Fleer et al., Polymers at Interfaces, Chapman, 1993, R. R. Netz, J. F. Joanny, Macromolecules, 32, 9013 (1999), A. V. Dobrynin, M. Rubinstein, Prog. Polym. Sci., 30, 1049-1118 (2005)] or these can be better harmonized with experimental findings on the dependence of the adsorbed quantity of PEL on the surface charge density.

By contrast, PEM are prepared by consecutive adsorption of polycations (PEL carrying positively charged functional groups or monomer units) with polyanions (PEL carrying negatively charged groups or monomer units) on a substrate, where the carrier is, for example, a silicon carrier, whose surface is treated chemically and/or physically [WO 2010 066432 A]. The cause of the adsorption and desorption is not isolated chemically and physically from the environment.

Polyelectrolyte complex particles (PEC) are formed at first by mixing a polycation and polyanion solution at a nonstoichiometric ratio in the volume phase [US 2008/0058229 A1]. The particles with neutral core and positively or negatively charged shell, which are formed in the process depending on the mixing ratio, can be bound to the charged carrier by physisorption similarly to the PEL.

PEM films can form oriented nanostructures by the use of rigid-chain PEL on, e.g., unidirectionally texturized carriers [M. Müller, Orientation of -helical Poly(L-lysine) in Consecutively Adsorbed Polyelectrolyte Multilayers on Texturized Silicon Substrates, Biomacromolecules, 2 (1), 262-269 (2001)].

Likewise, rod-shaped PEC particles, which can also produce oriented nanostructures on unidirectionally texturized carriers, can be formed by using rigid-chain PEL [M. Müller, T. Reihs, W. Quyang, Needle like and spherical polyelectrolyte complex nanoparticles of poly(L-lysine) and copolymers of maleic acid, Langmuir, 21 (1), 465-469 (2005)].

Oriented PEM films or PEC films can affect the cell growth and lead to the replacement of plasma-modified substrates, which can be prepared with a substantially greater effort.

Conductive PEL and polymers, e.g., polyaniline, polypyrrole, polythiophene or polyethylenedioxythiophene (PEDOT) can also be included and incorporated as single-component PEL materials or in PEM or PEC and used as conductive bonding agents between indium tin oxide (ITO) and active dye layers for organic light-emitting diodes (OLEDs).

These polyelectrolyte materials can, in turn, be used as bonding material for other materials, e.g., biomolecules and biomaterials, based on their structural relationship or even identity to biomaterials (proteins, polysaccharides, polynucleotides). Passivating layers that are inert in a controlled manner (PEL-1) or actively binding layers (PEL-2) or even biocidal layers (e.g., bacteria) (PEL-3) for biomaterials, biofluids or cells can thus form.

A question of current interest is the determination of the rate, strength and/or specificity of the binding, as well as the determination of the concentration of active biomolecules and particles as well as the identification of new interaction partners ("ligand fishing") on polyelectrolyte materials. Biomolecules may be hydrophobic or hydrophilic. Hydrophobic biomolecules are nonpolar. Hydrophilic biomolecules are polar and may have either positively charged (basic), negatively charged (acidic) charge centers (functional groups in contact with the solvent or be electrostatically neutral. Some low-molecular-weight biomolecules such as amino acids, monosaccharides and nucleotides are reactive monomers for the polymerization into high-molecular-weight biomolecules, the biopolymers such as proteins (e.g., collagen, serum albumin, insulin), polysaccharides (e.g., glycogen, starch, cellulose, dextrans, chitin) and polynucleotides (e.g., DNA, RNA).

FIG. 1 shows different, already electrically polarized or electrically polarizable biomaterials (BM), atoms, ions and/or molecules before (MA, MB, MC) and after the modification (MA', MB', MC'), single-component polyelectrolyte systems (PEE), polyelectrolyte multilayers (PEM) and polyelectrolyte complex articles (PEC). No distinction is made in the figures between polarizable biomaterials (BM), atoms, ions or molecules and single-component polyelectrolyte systems (PEE), polyelectrolyte multilayers (PEM) and polyelectrolyte complex particles (PEC). The lower part of FIG. 1 shows the structure of the polyelectrolyte materials (PEL) with a positive excess charge, and the upper part shows the structure of the PEL with a negative excess charge. These are shown in the further figures by an oval with a "+" or "−" corresponding to their excess charge. These electrically polarizable particles are designated by epAIMP. The epAIMP, which are shown schematically in different sizes and shapes, differ in terms of their electric polarizability, their mass and their tendency to bind with other biomaterials, atoms, ions and/or molecules or polyelectrolyte materials. The carrier according to the present invention utilizes the electric polarizability of the epAIMP, which is an indicator of the shiftability of positive charge relative to negative charge. Electron clouds can now be shifted relative to the positive heavy nucleus in atoms and ions and/or positive ions relative to negative ions in molecules. More complex epAIMP with higher electric multipoles may also appear and interact electrostatically with one another. Only electric dipoles are shown in the drawings for simplification.

The epAIMP may have a permanent electric dipole and/or form an electric dipole in electric fields. The dipole-dipole interactions of epAIMP ensure the orientation of the latter relative to one another. The electrostatic interaction belongs to the interactions with the strongest force and with the greatest range on the nanometer length scale. Electrostatic forces are also very strong in aqueous solutions and thus keep epAIMP away from each other. The epAIMP may occur not only as a dipole but also as a more complex epAIMP with higher electric multipoles and interact with one another electrostatically. Only electric dipoles are shown in the drawings for simplification.

Motion of the epAIMP is possible in electric fields between two electrodes, to which an electric voltage is applied from the outside.

Individual mobile ions can be moved in a solid with rear-side electrode and with static or positionable front-side electrode, e.g., the metallically conductive measuring tip of an Atomic Force Microscope [N. Balke et al.: Nanoscale mapping of ion diffusion in a lithium-ion battery cathode. NATURE NANOTECHNOLOGY 5 (2010), 749-754].

Outside a solid, epAIMP can be moved by dielectrophoresis [Pei Yu Chiou et al.: Massively parallel manipulation of single cells and microparticles using optical images. NATURE 436 (2005) 370-372] between the surface of a carrier and a large-area front-side electrode, which is arranged at a spaced location from the surface of the carrier and does not touch this. The rear side of the carrier is illuminated for this through a shadow mask. The photogenerated charge carriers in the carrier locally increase the conductivity of the carrier and locally shift the position of the rear-side electrode from the lower ITO layer into the undoped a-Si:H of the carrier. The distance between the upper ITO layer (front-side electrode) with unchanged position and the rear-side electrode with variable position is locally changed hereby. The voltage dropping between the front-side electrode and the rear-side electrode causes a locally varying electric field. The direction of the electric field is determined by the polarity of the voltage applied to the front-side electrode and the rear-side electrode. Different positions of the rear-side electrode can be set on the micrometer scale very rapidly by changing the shadow mask.

A molecular machine is constructed from a discrete number of epAIMP and assumes special functions on the nanometer and/or micrometer length scale. Its mode of operation is similar in many respects to that of the machines created by humans. It is a mechanism in which individual parts fit into one another, move and interact in order to perform a certain task [Goodsell, David S.: Wirtschaft and Produktion in der molecularen Welt [Economy and Production in the Molecular World], Translated by Hummel, Isolde, 2nd ed., 2010. Spektrum Akademischer Verlag].

Molecular machines produce a mechanical motion (output) as a response to a specific stimulus (input). There are artificial and biological molecular machines.

All molecules that transmit functions from the meter length scale to the nanometer and/or micrometer length scale and perform same are called molecular machines in the broadened sense of the word.

The epAIMP for building the molecular machines exists in a small number of forms and sizes only. For example, artificial molecular machines can be built up from rotaxanes and catenanes Biological molecular machines are built up largely from six types of atoms, namely, carbon, oxygen, nitrogen, sulfur, phosphorus and hydrogen, as well as largely from four types of molecules, namely, proteins, nucleic acids, lipids and polysaccharides.

When atoms, ions and/or molecules meet each other, they interact with one another. If this interaction is weak, e.g., in slow neutral gases, the atoms and/or molecules continue their paths unchanged after the collision. If the interaction is strong, e.g., in gases containing ions or in fast neutral gases, the atoms, ions and/or molecules continue their paths in a changed form after the collision, during which coulomb forces may act between ions and resonant charge transfer may act between neutral atoms and molecules.

The discrete number of atomic, ionic and/or molecular components is composed into artificial and biological molecular machines, which are always tailored optimally to a certain role, according to a blueprint by means of the basic concepts, namely, chemical complementarity and hydrophobicity.

If the interaction is complementary, e.g., if atomic and molecular areas fit perfectly into a similarly shaped atomic and molecular area of an adjacent molecule, a solid bond is formed.

Molecular machines use two special types of bonds: Hydrogen bridges between a hydrogen atom and an oxygen or nitrogen atom, as well as salt bridges between atoms, ions, and/or molecules, which carry an opposite electric charge. These special bonds function like small clamps, which couple atoms, ions and molecules with one another.

The formation of a special type of bond can be catalyzed by a modification of the epAIMP.

A large-area modification of heat-sensitive epAIMP can be brought about by supplying heat. The heat energy can be produced, e.g., by reversing the magnetic poles of magnetizable particles in a magnetic field applied from the outside [US 2008 0319247 A1], by absorption of electromagnetic waves and/or by excitation of lattice vibrations by laser pulses of a pulse length of 10 nanosec with an energy density of 20 W/mm2 [M. E. Msall et al.: Ballistic phonon production in photoexcited Ge, GaAs, and Si. PHYS. REV. B. 65 (2002), 195205-1-7].

The simple artificial molecular machines already synthesized include motors [Javier Vicario et al.: Controlling the speed of rotation in molecular motors. Dramatic acceleration of the rotary motion by structural modification, CHEM. COMMUN. (2005), 5910-5912], propellers [B. Wang et al.: Chemically Tunable Nanoscale Propellers of Liquids. PHYS. REV. LETT., 98 (2007), 266102-1-4], switches [Jean-Pierre Desvergne et al.: Cation complexing photochromic materials involving bisanthracenes linked by a polyether chain. Preparation of a crown-ether by photocycloisomerization; J. CHEM. SOC., CHEM. COMMUN. (1978), 403-404], molecular transporters, molecular pincers, molecular sensors and logic elements [Jonathan E. Green et al.: A 160-kilobit molecular electronic memory patterned at 1011 bits per square centimeter. NATURE, 445 (2007), 414-417].

The manufacture of molecular machines is an essential prerequisite for current research in the field of molecular assembling, DNA machines, nanoelectromechanical systems, nanosensors and protein dynamics.

Complex molecular machines were already designed theoretically, but could not be tested as yet, because there are no methods so far for manufacturing complex molecular machines.

Molecular sensors interact with an analyte and indicate a measurable change. Fluorescences in ether radicals on molecular sensors are frequently used to measure the change after interaction.

The carriers developed so far are not suitable for taking up, modifying and moving individual epAIMP in a manner limited in space and time. No molecular machines can be manufactured with the hitherto known carriers from the electrically polarizable atoms, ions, molecules, biomaterials or polyelectrolyte materials.

The direction of the electric field at a given point in time is the same everywhere during electrophoresis [Pei Yu Chiou et al.: Massively parallel manipulation of single cells and microparticles using optical images. NATURE, 436 (2005), 370-372]. The photogenerated charge carriers also diffuse into the undoped a-Si:H in case of excessively long illumination of the rear-side electrode, they increase the conductivity of the undoped a-Si:H everywhere and thus shift the position of the rear-side electrode over a large area from the lower ITO layer into the undoped a-Si:H. In addition, the application of an electric voltage between the front-side electrode, which is located at a spaced location from the surface of the carrier (nitride layer), and the rear-side electrode, is disadvantageous, because the distance between the nitride layer and the front-side electrode must be greater than the particles or cells in order for the latter to be able to move mechanically freely on the nitride layer.

The propagation of the electric field between the front-side electrode and the rear-side electrode is not homogeneous during electrophoresis, because the particles and/or cells pass on the electric field lines differently due to their dielectric properties than does the surrounding material. The particles and/or cells thus affect the electric field, which shall actually be used to affect the particles and/or cells.

Smaller particles and/or cells (<1 micrometer) cannot be sorted during electrophoresis, because the localization of the rear-side electrode is limited due to the diffusion of the photogenerated charge carriers and because the electric field between the front-side electrode and the rear-side electrode is not large enough to overcome the Brownian motion of the particles and/or cells.

The detection of the localized particles and/or cells can be carried out during electrophoresis only optically through the front-side electrode. If the front-side electrode is taken away, no electric field will develop and the particles and cells cannot be localized. Detection of the localized particles by means of atomic force microscopic measurements or by means of scanning electron microscopic measurements is not possible through the front-side electrode.

SUMMARY OF THE INVENTION

The object of the present invention is to propose a carrier for the manipulation, modification and motion of electrically polarizable biomaterials, atoms, ions, molecules or polyelectrolyte materials. The carrier shall guarantee locally controllable adsorption and desorption of the materials.

The polyelectrolyte material may consist of multicomponent polyelectrolyte multilayers (PEM) or preformed polyelectrolyte complex particles (PEC). The preparation and the possible embodiment variants of the carrier, e.g., for the local manipulation and modification and for the translatory and/or rotatory transport of individual epAIMP as well as the use of the carrier for the spatially and temporally limitable uptake of the epAIMP for manufacturing molecular machines mM shall be described. The adhesion (adhesiveness) of epAIMP on the carrier as well as the mobility of the epAIMP play an important role here. The adhesion and the mobility of epAIMP shall be controlled by the carrier.

The starting point for the carrier is a locally doped semiconductor material or a piezoelectric or ferroelectric material. An insulating cover layer may be optionally applied to the surface. The carrier is a source of locally controllable, near-surface electrostatic forces, which can manipulate, modify and/or move the epAIMPs. Contrary to the current state of the art, these near-surface electrostatic forces are not affected by the environment, and the near-surface electrostatic forces are chemically isolated from the environment.

The epAIMP can be oriented by near-surface electrostatic forces of different strengths or can be oriented to or up to a few nanometers above the surface of a carrier or to other epAIMP, which are close to the surface of the carrier or are added to the surface of the carrier.

The high surface charge density of the carriers leads, in general, to a larger adsorbed quantity of epAIMP, e.g., of single-component PEL materials, of PEM and PEC systems compared to other substrates (e.g., silicon-water). The direction and strength of the near-surface electrostatic forces on the surface of the carrier is varied by selecting the species (electrons or holes) and/or the concentration of the majority charge carrier in the locally doped semiconductor or by forming domains in the piezoelectric or ferroelectric material. Space charge densities of $10^{15}$ to $10^{21}$ $e/cm^3$ and surface charge densities of $10^{10}$ to $10^{14}$ $e/cm^2$ are reached in the semiconductor by doping. The surface charge density in piezoelectric and ferroelectric materials equals $10^{13}$ to $10^{15}$ $e/cm^2$.

The thickness of the insulating cover layer and/or the local charges in the insulating cover layer determine the strength of the near-surface electrostatic forces. The range of the electrostatic forces reaches up to 100 nm above the surface of the carrier. The adsorbed quantity of the epAIMP can thus be set in a controlled manner by selecting the thickness of this cover layer.

The structuring of the insulating cover layer and/or of the subjacent semiconductor or piezoelectric or ferroelectric material determines the direction and extent of the near-surface electrostatic forces. Thus, epAIMP materials can be deposited in a structured or locally controlled manner.

Structured single-component and PEL, multicomponent PEM and PEC layers, biomaterials, ions, atoms and molecules (epAIMP) are manipulated, i.e., adsorbed or desorbed, by changing the direction and strength of near-surface electrostatic forces by applying a voltage to the rear-side electrode of the carrier.

Transition areas with reversed direction of the near-surface electrostatic forces can be formed in the carrier in a specific manner and can be used by applying a voltage to one or more rear-side electrodes of the carrier to manipulate the epAIMP.

By using the formation of intrinsic electric fields in the space charge zones (transition areas in the semiconductor) of local doping profiles, an even more intense manipulation of the near-surface electrostatic forces can be carried out by applying a voltage to the rear-side electrode. The adsorption of the epAIMP can thus be controlled as well.

The generation of domains with reversed direction of the near-surface electrostatic forces in the piezoelectric or ferroelectric material (transition areas in the piezoelectric or ferroelectric material) is carried out by local structuring of the piezoelectric or ferroelectric material.

An optically active material may be used as an insulating layer, as a semiconductor material or as a piezoelectric or ferroelectric material, and/or a magnetizable material may be used as a charged imperfection in the carrier for the specific local excitation or adsorption of epAIMP.

A crossbar structure can be obtained for the local sorting and manipulation of epAIMP by structuring the rear-side electrode as well as of the implanted areas.

The carrier may be formed from individual carrier cells of the array without gaps and free from overlapping by different polygons and each carrier cell or individual carrier cells are provided with a metallically conducting rear-side electrode of its/their own. A tetragonal polygon structure will be assumed below for a simpler description and use of the array structure according to the present invention.

By using the formation of electric gradient fields in the near-surface area of the carrier, the epAIMP can be manipulated even more strongly by the application of a voltage to the rear-side electrode by means of near-surface electrostatic forces.

The formation of strong electric gradient fields may take place at the boundary between p-type semiconductor p and n-type semiconductor n or at the boundary between domains with oppositely directed intrinsic electric fields.

The production of p-type semiconductors p and n-type semiconductors n can be carried out by means of ion implantation and subsequent heat curing.

Transition areas between adjacent carrier cells with respective opposite directions of the near-surface electrostatic forces can be formed in a specific manner in the carrier and used to transport individual epAIMP within individual carrier cells and between adjacent carrier cells by applying a voltage to one or more rear-side electrodes of the carrier.

Localized, temperature-sensitive epAIM can be modified on the carrier cells by applying an external magnetic field and the evolution of heat when reversing the magnetization of the magnetic particles by introducing magnetizable nanoparticles or microparticles into the insulating layer or into the near-surface area of said individual carrier cells.

The carrier with different electron-phonon interaction properties of the individual carrier cells can be illuminated over a large area for the local excitation of lattice vibrations. Based on the electron-phonon interaction, the conversion of light energy into lattice vibration energy is greatest in the carrier cells with a strong electron-phonon interaction.

Molecular machines can be manufactured by the sequential transport of epAIMP to the carrier cells at which the molecular machines are formed. Individual epAIMP may be optionally modified before/after/during the transport. This modification may be carried out to catalyze the connection between epAIM, from which the molecular machines are formed.

One main advantage is the compatibility of the carrier with microelectronics and the use of a chemically resistant and biocompatible insulating cover layer as well as the reusability of the carrier. Another advantage is the fact that the manipulation, modification and transport of individual epAIM is variable in time and/or space. The area of the carrier from which the near-surface electrostatic forces originate based on the redistribution of charges in the near-surface area of the carrier is completely separated from the adsorbed epAIMP in space and chemically. This means that only the near-surface electrostatic forces act, but there is no direct contact with the charges in the near-surface area of the carrier. The epAIM from which molecular machines mM are composed can be filtered from gases, liquids and powders by specific attraction to the carrier and later repulsion from the carrier. The slip-stick mechanism can be used, utilizing the dynamics of motion, for sorting epAIMP with different masses and different electric polarizability.

Another advantage is the availability of the epAIMP, especially of the PEL materials, and the use of simple wet chemical processes with water as the solvent. Other solvents may be used as well.

Another advantage is the infinitely variable surface charge density, if the carrier is a semiconductor, and the surface charge density that can be regulated by increments, if the carrier is a piezoelectric or ferroelectric material. If the adsorption of epAIMP, for example, PEL materials, depends directly on the charge density, controlled deposition of epAIMP can thus be achieved.

Another advantage is the fact that the adsorption and desorption are variable in time and/or space, i.e., components can be filtered with the carriers modified by the epAIMP from liquids or mixtures by specific attraction (adsorption) to the carrier and later repulsion (desorption) from the carrier.

Another advantage is the exclusive structurability of the near-surface areas of the carrier by electrostatic forces and surface charge concerning the sign and amplitude thereof, without other surface properties, such as roughness, morphology, wetting, concentration and composition of functional groups, undergoing any change Only the short-range van der Waals forces of the insulating cover layer and the long-range, near-surface electrostatic forces of the surface charge will always act on the epAIMP. This has advantages because only one parameter, the surface charge, must be taken into account during the quantitatively and locally controlled deposition of epAIMP.

In particular, unidirectionally oriented charge patterns can be produced via the carriers and these can be used as a template for the selective adsorption and orientation of epAIMP, for example, of PEL materials from rigid-chain PEL. Advantages are expected over mechanical texturing methods or texturing methods based on mechanical stretching.

Such surfaces of the carriers, which are modified and structured in a specifically unidirectional manner according to paragraph [0081] and are modified and structured in a pattern-controlled manner with epAIMP according to paragraph [0082], can lead to a unidirectionally directed or selective interaction or to the same growth of cells.

Based on the chemical isolation of the cause of the electrostatic forces from the environment, chemical reactions that may possibly take place and thus an influence on the electrostatic forces are avoided. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
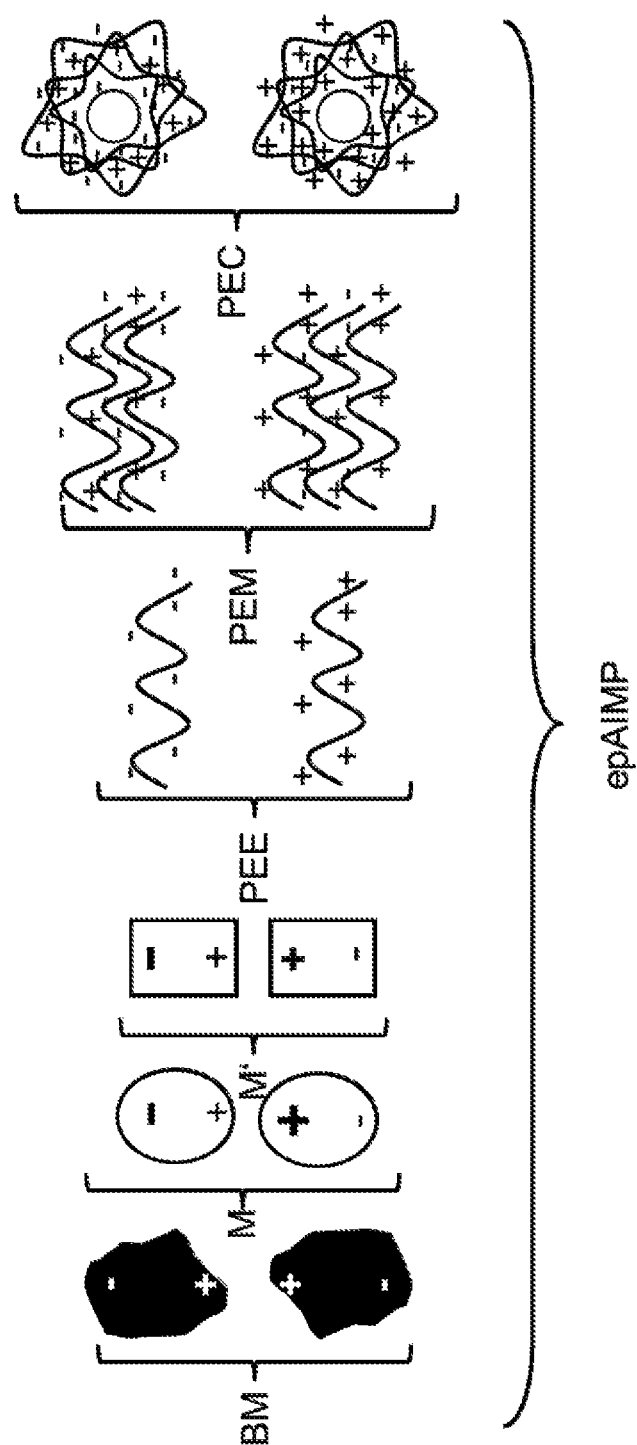
FIG. 1 is a view showing different, already electrically polarized or electrically polarizable biomaterials.

Referring to the drawings in particular, a carrier comprising a semiconductor material, for example, silicon, with insulating cover layer 1, wherein the near-surface electrostatic forces are determined by the local doping of the semiconductor with donors or acceptors and by the thickness of the insulating cover layer. It is sufficient, as a rule, if the semiconductor material has a thickness of at least 1 μm and the insulating cover layer has a thickness of about 2 nm to 3 nm. This carrier can be used as a biochip.

By applying at least one rear-side electrode to the semiconductor material, the biochip can be used as a reusable filter. By changing the voltage applied to the rear-side electrode, it is possible now to consecutively repel or detach different epAIMP added to the carrier and to quantify the detached epAIMPs after the detachment step. The quantification may take place without markers and electrically by means of electron beams (23,24) from an electron source 25 by an electron detector 26.

An area-covering subdivision of the carrier with insulating cover layer into overlapping areas with different near-surface electrostatic forces makes possible a specific manipulation, modification and motion of different epAIMP on the surface of the carrier. A rear-side contact of its own is ideally arranged on each carrier cell TMZ(i,j).

Figure 2:
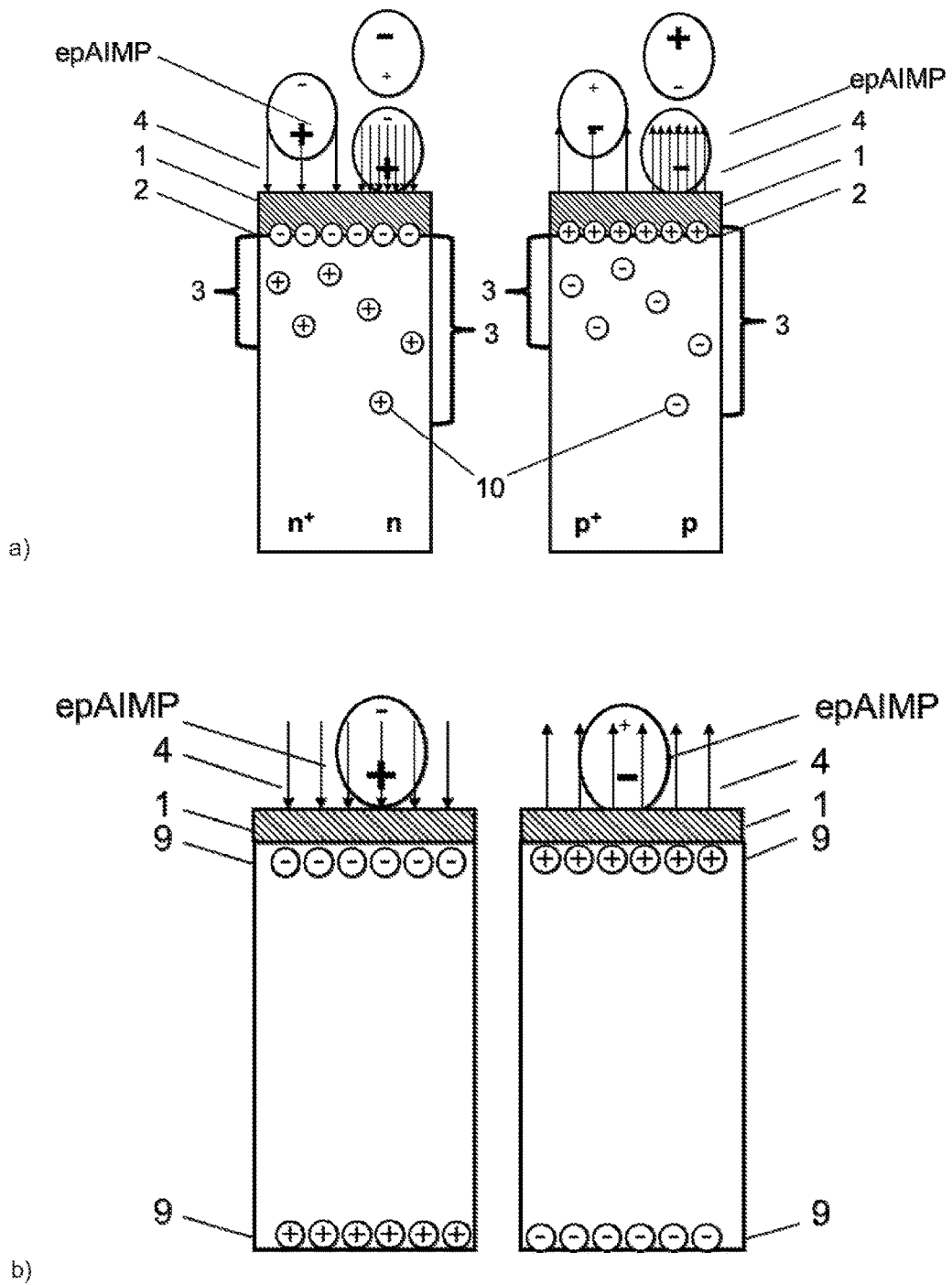
FIG. 2 shows a carrier TM consisting of semiconducting (a) and from piezoelectric or ferroelectric (b) material with near-surface electrostatic force (4) (a) of different strength and (b) of equal strength.

FIG. 2 a) shows the use of the carrier according to the present invention as a semiconducting, locally doped p-type semiconductor p, $p^+$ and/or n-type semiconductor n, $n^+$ with preferably locally different acceptor concentration $N_A$ in the p-semiconductor and with preferably locally different donor concentration $N_D$ in the n-type semiconductor, wherein the semiconductor may also be undoped. An insulating cover layer 1 is preferably located on the semiconductor surface. Occupied interface states of a number G are formed between the insulating cover layer 1 and the n-type semiconductor or the p-type semiconductor. Furthermore, G acceptors are unshielded 10 and ionized (−) in the near-surface area of the p-type semiconductor and G donators are unshielded 10 and ionized (+) in the n-type semiconductor. The occupied interface states and the unshielded acceptors and donors form an asymmetrical electrostatic dipole 3. The senses of direction of the near-surface electrostatic forces 4 of the asymmetric electrostatic dipole 3 over a p-type semiconductor p and over an n-type semiconductor n are opposite each other. The strength of the near-surface electrostatic force 4 over the p-type semiconductor increases with decreasing acceptor concentration $N_A$ and that over the n-semiconductor increases with decreasing donor concentration $N_D$. The properties of the interface between the semiconductor material and the insulating cover layer concerning the state density and time constant of the interface states can be set specifically by physical, chemical or thermal pretreatment of the semiconductor surface prior to the application of the insulating cover layer 1.

FIG. 2 *b*) shows the use of the carrier according to the present invention as a piezoelectric or ferroelectric material with the polarization charge 9 on the top side and underside of the piezoelectric or ferroelectric material. An insulating cover layer 1 is preferably located on the surface of the piezoelectric or ferroelectric material. The sense of direction of the near-surface electrostatic forces 4 is determined by the sign of the polarization charge 9 on the top side and the underside of the piezoelectric or ferroelectric material. The strength of the near-surface electrostatic forces 4 increases with increasing number of polarization charges 9 per area unit up to a material-dependent saturation value. The strength of the near-surface electrostatic forces 4 increases with increasing distance of the polarization charges 9 between the top side and the underside of the piezoelectric and ferroelectric material up to a material-dependent saturation value.

Figure 3:
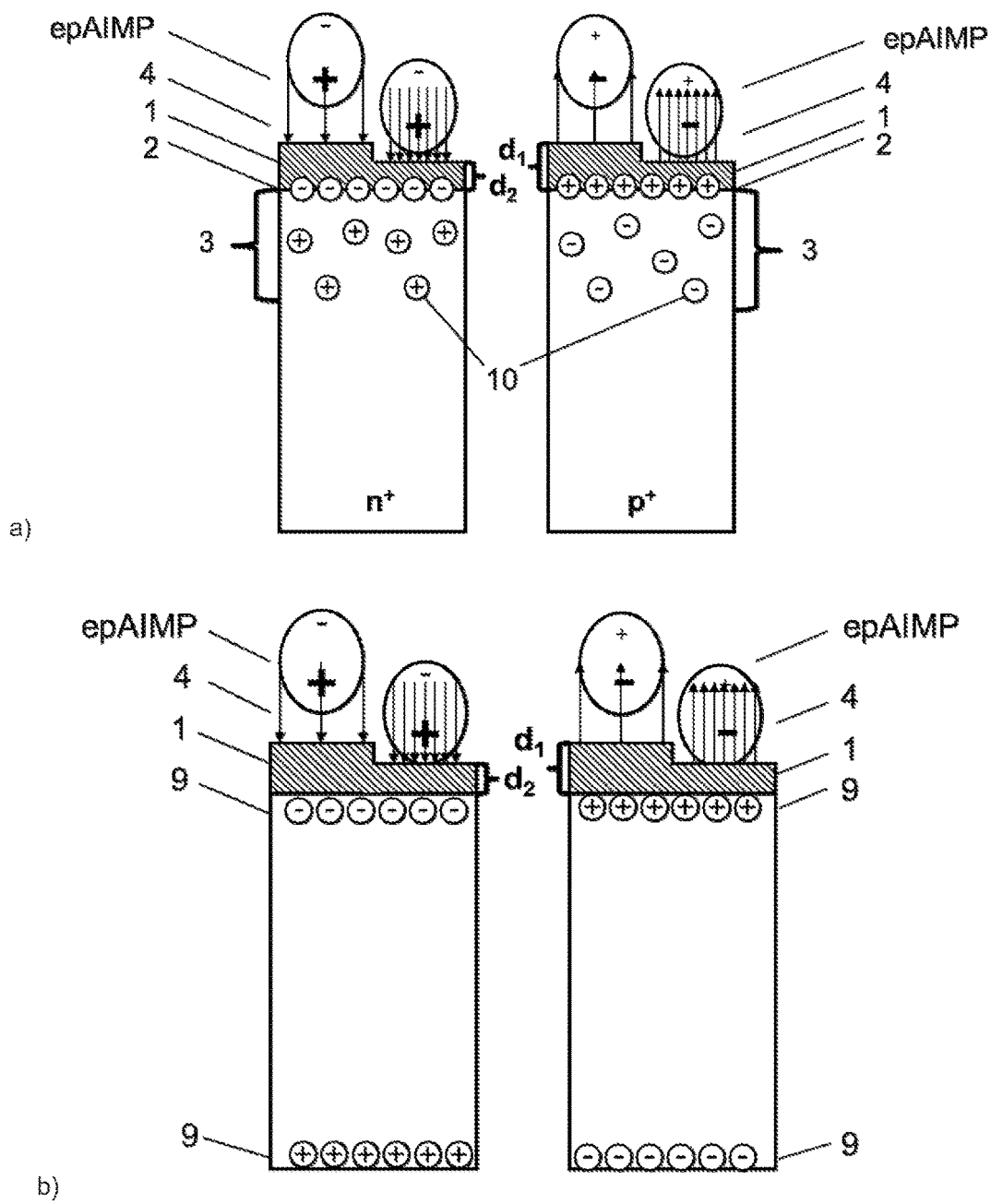
FIG. 3 is a view showing a carrier TM consisting of semiconducting (a) material and of piezoelectric or ferroelectric (b) material with structured insulating cover layer (1) with near-surface electrostatic force (4) with different strengths.
Figure 4:
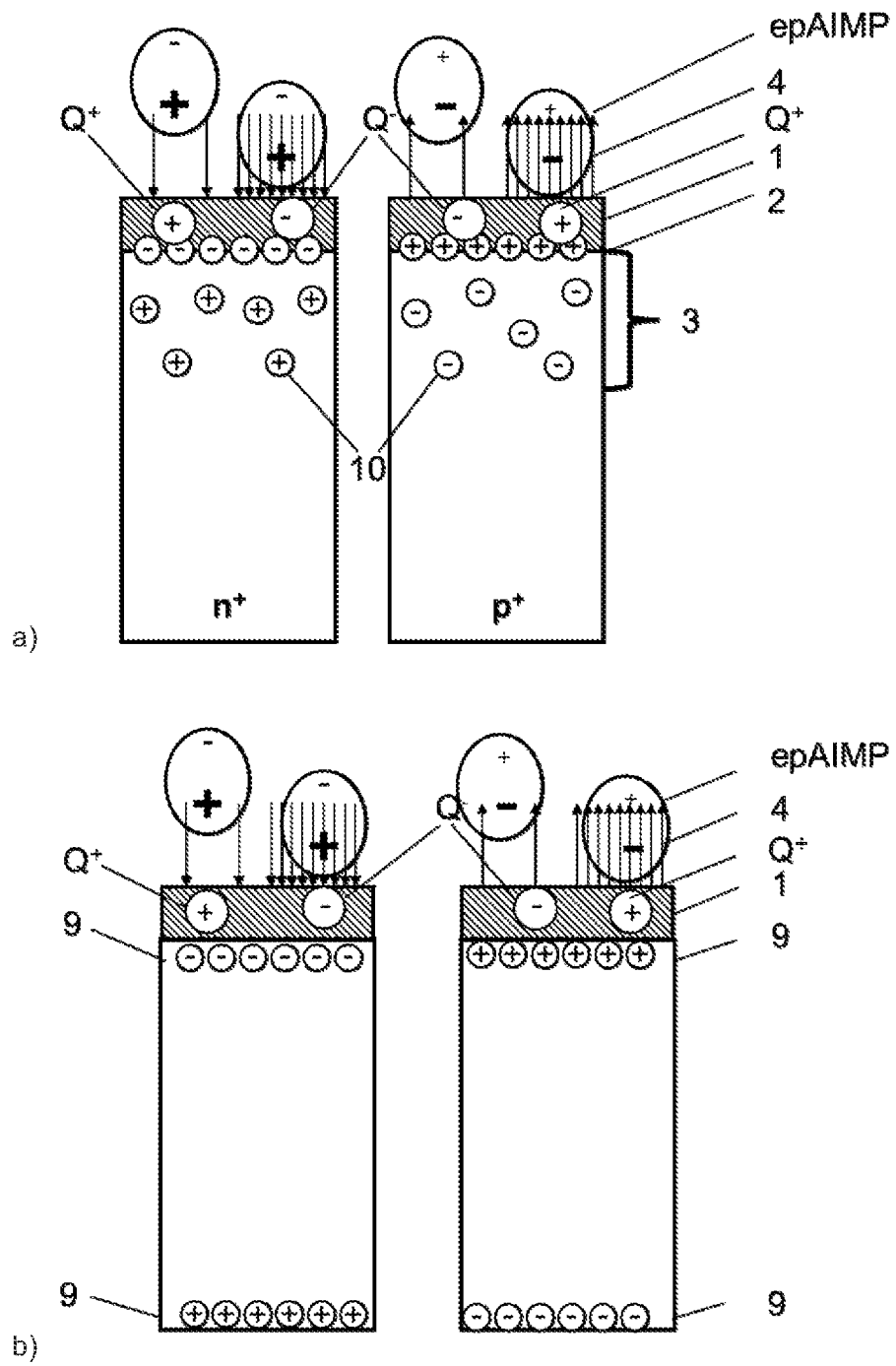
FIG. 4 is a view showing a carrier TM consisting of semiconducting (a) material and piezoelectric or ferroelectric (b) material with insulating cover layer (1) with charged imperfections in the insulating cover layer (1)
Figure 5:
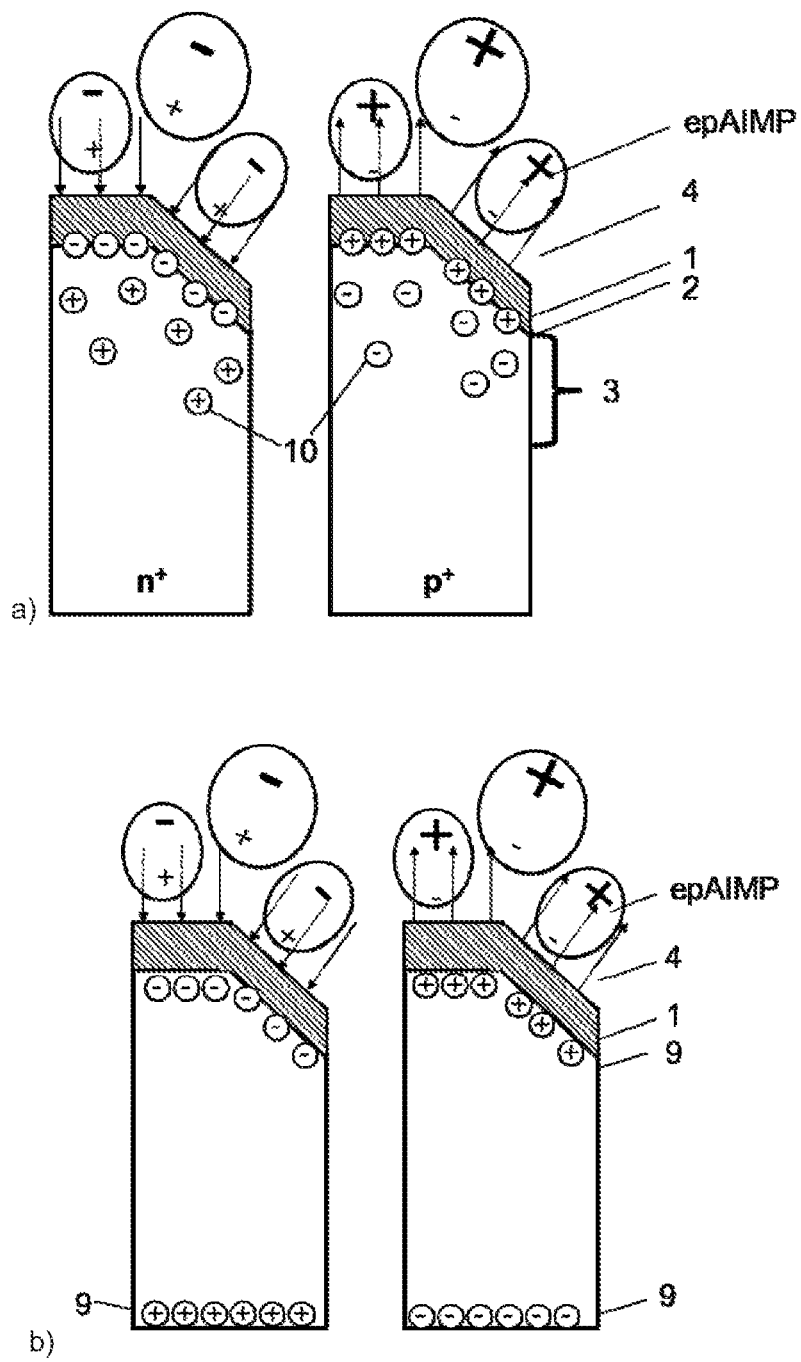
FIG. 5 is a view showing a carrier TM consisting of structured, semiconducting (a) material and structured, piezoelectric or ferroelectric (b) material with insulating cover layer (1) with near-surface electrostatic force (4) with different directions and equal strength.

FIG. 3 is a view showing a carrier TM consisting of semiconducting (a) material and of piezoelectric or ferroelectric (b) material with structured, insulating cover layer (1) with near-surface electrostatic force (4) with identical sense of direction and different strengths.

Besides the selection of the species (p or n) and the concentration of the majority charge carriers ($N_A$ or $N_D$), the near-surface electrostatic forces (4) can be varied locally by a local variation of the thickness $d_i$ of the insulating cover layer 1 (FIG. 3 *a*). The electrostatic forces 4 increase with decreasing thickness $d_i$ of the insulating cover layer 1. The local modification of the thickness d of the insulating cover layer 1 can be performed by photolithography.

The near-surface electrostatic forces (4) over a carrier with piezoelectric or ferroelectric material can be varied locally by the local variation of the thickness $d_i$ of the insulating cover layer 1 (FIG. 3 *b*). The electrostatic forces 4 increase with decreasing thickness $d_i$ of the insulating cover layer 1. The local modification of the thickness d of the insulating cover layer 1 may be carried out by means of photolithography.

The insulating cover layer 1 may be a high-k or low-k oxide. The corresponding oxide of the semiconductor material may be used, for example, in a carrier TM consisting of semiconducting material. For example, silica or aluminum oxide may be used in a carrier consisting of piezoelectric or ferroelectric material. Moreover, biocompatible materials with a great energy gap $E_g$, such as zinc oxide or titanium dioxide, are possible as an insulating cover layer 1.

Figure 6:
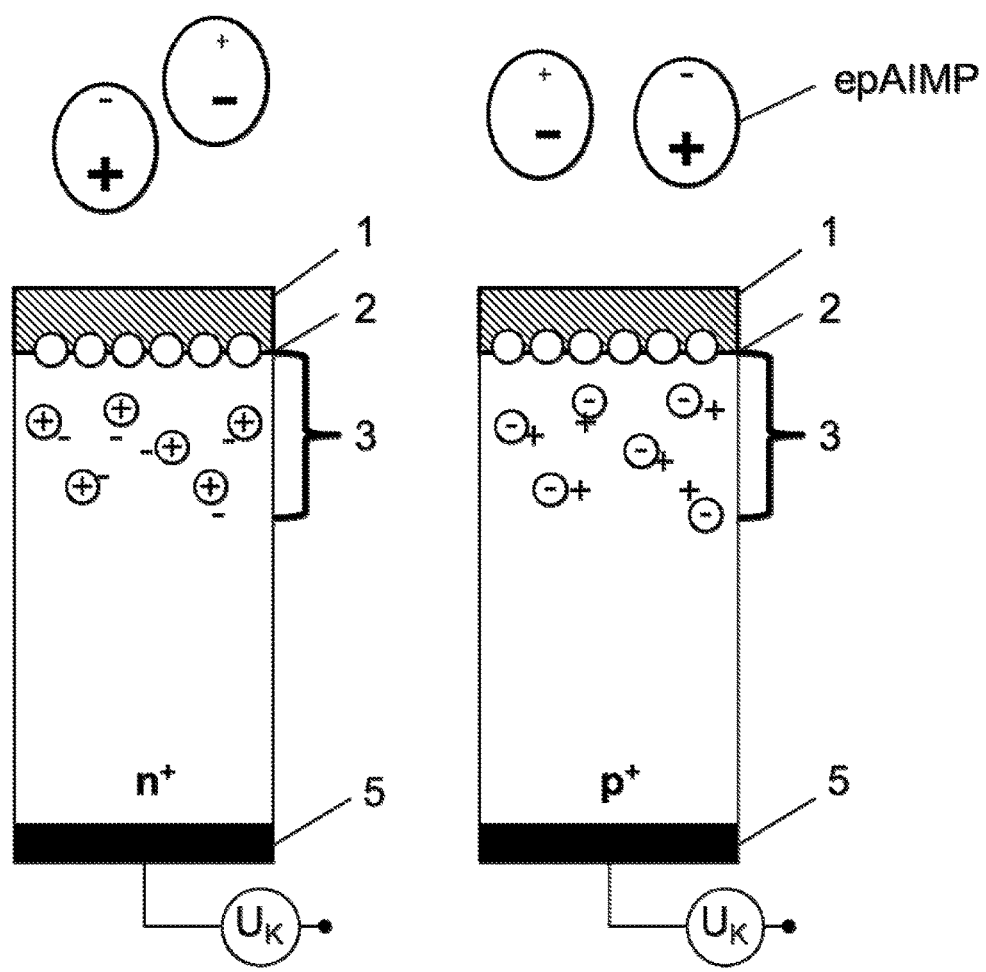
FIG. 6 is a view showing a carrier TM consisting of semiconducting material with insulating cover layer (1) with metallically conducting rear-side electrode (5) and minimized near-surface electrostatic force (4) by application of a direct voltage (Kelvin voltage)

FIG. 4 shows the use of charged imperfections $Q^+$ or $Q^-$ in the insulating cover layer (1) for reducing or increasing the near-surface electrostatic forces and hence for the specific modification of the attracting and repelling forces acting on the epAIMP.

The near-surface electrostatic forces 4 of the asymmetric electrostatic surface dipole 3 can be reduced or increased by positive (+) charges $Q^+$ and/or negative (−) charges $Q^-$, by so-called oxide charges in the insulating cover layer 1 (FIG. 4 *a*). The near-surface electrostatic forces 4 are thus reduced, for example, when introducing negative charges $Q^-$ in the insulating cover layer 1 via a p-type semiconductor p, whereas positive charges $Q^+$ in the insulating cover layer 1 [introduced] via a p-type semiconductor p increase the near-surface electrostatic forces 4. On the other hand, the near-surface electrostatic forces 4 are increased when introducing negative charges $Q^-$ in the insulating cover layer 1 via an n-type semiconductor n, whereas positive charges $Q^+$ in the insulating cover layer 1 introduced via an n-type semiconductor reduce the near-surface electrostatic forces 4.

The near-surface electrostatic forces 4 of the polarization charge 9 on the top side and underside of the piezoelectric or ferroelectric material can be reduced or increased by positive (+) charges $Q^+$ and/or negative (−) charges $Q^-$, by so-called charged imperfections in the carrier, preferably in the insulating cover layer (FIG. 4 *b*). The near-surface electrostatic forces 4 are thus reduced, for example, when introducing negative charges $Q^-$ in the insulating cover layer 1 over a piezoelectric or ferroelectric material with positive polarization charge 9 on the top side of the piezoelectric or ferroelectric material, whereas positive charges $Q^-$ in the insulating cover layer 1 over a piezoelectric or ferroelectric material with positive polarization charge 9 on the top side of the piezoelectric or ferroelectric material increase the near-surface electrostatic forces 4. The charged imperfections $Q^+$ and $Q^-$ used may optionally be introduced additionally or in the semiconductor material or in the piezoelectric or ferroelectric material only.

The charged imperfections $Q^+$ and $Q^-$ used may be additionally magnetizable and thus be activated by a magnetic field 14 applied from the outside.

The direction of the near-surface electrostatic forces 4 can be modified by structuring the surface of the n-type semiconductor n and/or of the p-type semiconductor p, e.g., by means of photolithography, electron beam lithography and/or ion beam lithography, preferably prior to the application of the insulating cover layer 1 (FIG. 5 *a*). The near-surface electrostatic force 4 is preferably directed at right angles to the surface in an unstructured semiconductor surface. The direction of the near-surface electrostatic forces 4 determines the orientation of the epAIMP on the surface of the carrier TM.

The direction of the near-surface electrostatic forces 4 can be modified by structuring the surface of the piezoelectric or ferroelectric material, e.g., by means of photolithography, electron beam lithography and/or ion beam lithography, preferably prior to the application of the insulating cover layer 1 (FIG. 5 *b*). The near-surface electrostatic force 4 is preferably directed at right angles to the surface in an unstructured surface of the piezoelectric or ferroelectric material. The direction of the near-surface electrostatic forces 4 determines the orientation of the epAIMP on the surface of the carrier TM.

A metallically conducting rear-side electrode 5 is applied to the rear side of the doped semiconductor for manipulating the epAIMP on the surface (FIG. 6). A direct voltage $U_K$ is applied to the rear-side electrode 5. It is important that the near-surface electrostatic forces 4 be minimized or reduced to zero by the application of a suitable direct voltage $U_K$. The near-surface electrostatic forces 4 are reduced to zero in FIG. 6. The suitable direct voltage $U_K$ corresponds to the energy gap between the position of the Fermi level, which depends on the donor concentration $N_D$, and the conduction band edge $E_C$ in the n-type semiconductor n and/or the energy gap between the position of the Fermi level, which depends on the acceptor concentration $N_A$, and the valence band edge $E_V$ in the p-type semiconductor p, for example, in the semiconductor material silicon. The rear-side electrode 5 is preferably applied over a large area. The near-surface electrostatic forces 4 can be extinguished with this arrangement.

Figure 7:
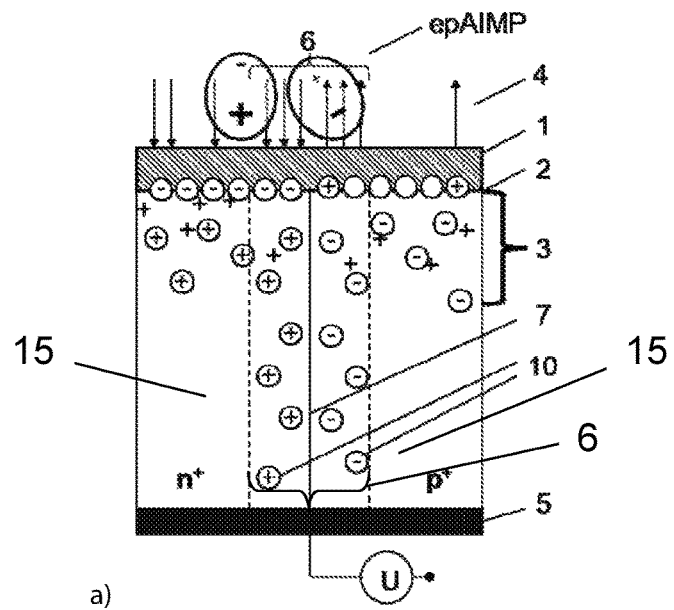
FIG. 7 is a view showing a carrier TM with large-area, metallically conducting rear-side electrode (5) consisting of semiconducting material (a) with holes (p+) and with electrons (n+) and with the boundary (7) between n-semiconductor and p-semiconductor and of piezoelectric or ferroelectric material (b) with domains with oppositely directed intrinsic electric fields and with the boundary between domains with oppositely directed intrinsic electric fields (8b)
Figure 7:
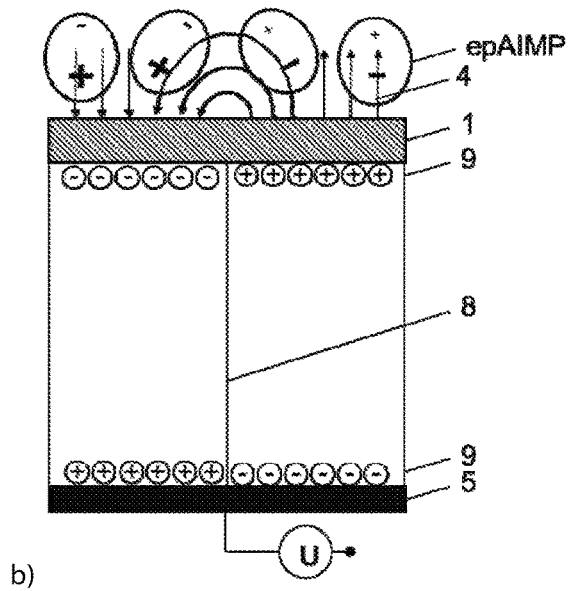

The semiconductor is doped such (FIG. 7a) that differently doped areas of the semiconductor meet at interfaces 7. An area (space charge zone) 6, which contains no free charge carriers (only unshielded doping atoms 10), is formed at such interfaces 7. An electric field, whose maximum is located in the interface 7 and which is zero at the edge of the space charge zone 6, is formed at right angles to the interface 7. A metallically conducting rear-side electrode 5 is applied to the rear side of the doped semiconductor for a time-dependent manipulation (FIG. 7 a) of the epAIMP. A voltage U is applied to the rear-side electrode 5. The voltage U may be a superimposition of an alternating voltage and a direct voltage. The near-surface electrostatic forces 4 are minimized and maximized as a function of the time by applying the voltage U. The rear-side electrode 5 is preferably applied over a large area. The electric fields at right angles to the interface 7 do not necessarily extend parallel/antiparallel to the electric field, which is formed by the application of the voltage U to the rear-side electrode 5 between the rear-side electrode 5 and the surface of the semiconductor. It is important that a separate time-dependent manipulation of the epAIMP be possible near interfaces 7 based on the near-surface electrostatic forces in the transition area 6, because the shift of free charge carriers in the space charge zone 6 of the semiconductor is affected by intrinsic electric fields when the voltage U is applied. The transition region 6 is formed between two adjacent regions 15.

The piezoelectric or ferroelectric material is structured such (FIG. 7 b) that different areas of the piezoelectric or ferroelectric material with different polarization charge 9 (domains) on the top side and underside of the piezoelectric or ferroelectric material meet at the interface 8. The directions of the near-surface electrostatic forces above left and above right of such interfaces 8 are opposite. The near-surface electrostatic forces above such interfaces 8 do not necessarily extend at right angles to the surface of the carrier but they rather pass continuously one over into the other.

Figure 8:
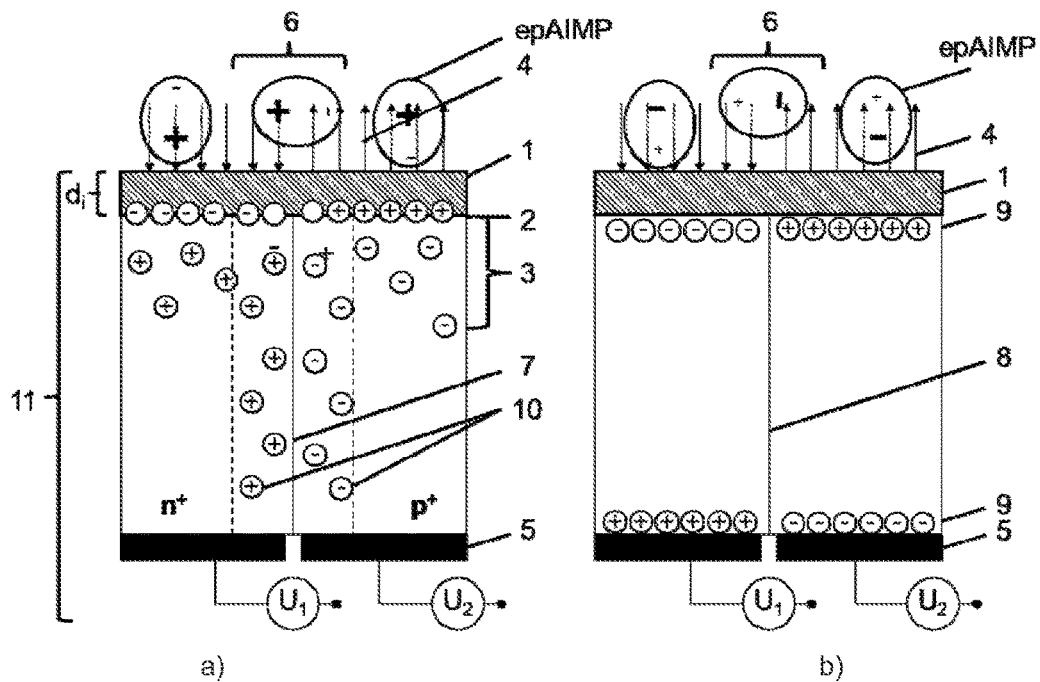
FIG. 8 is a view showing a carrier TM consisting of semiconducting material (a) with holes (p) and with electrons (n) and with the boundary (7) between n-semiconductor and p-semiconductor and of piezoelectric or ferroelectric material (b) with domains with oppositely directed intrinsic electric fields and with the boundary between domains with oppositely directed intrinsic electric fields 8 with structured, metallically conducting rear-side electrode (5)

A structured metallically conducting rear-side electrode 5 is applied to the rear side of the doped semiconductor for a strongly time-dependent manipulation (FIG. 8 a) of the epAIMP on the surface. A voltage $U_i$, in which $I=1, \ldots, m$, in which m indicates the number of rear-side electrodes 5, is applied to the structured rear-side electrode 5. Voltage $U_i$ is a superposition of an alternating voltage and a direct voltage. The near-surface electrostatic forces 4 are controlled independently from one another in the different areas by applying the voltages $U_i$. The formation of structured, near-surface electrostatic forces 4 may also be set by the structured implantation of the semiconductor, e.g., by an orientation of semiconductor areas implanted in a strip-shaped manner and of rear-side electrode areas 5 structured in a strip-shaped pattern, which orientation is rotated by 90° in relation to one another (crossbar array).

A structured, metallically conducting rear-side electrode 5 is applied to the rear side of the piezoelectric or ferroelectric material for a strongly time-dependent manipulation (FIG. 8 b) of the epAIMP on the surface. A voltage $U_i$ is applied to the structured rear-side electrode. Voltage $U_i$ is a superposition of an alternating voltage and a direct voltage. The near-surface electrostatic forces 4 are controlled independently from one another in the different areas by the application of the voltages $U_i$.

The near-surface electrostatic forces over the interface 8 are especially strong in the transition area 6 and epAIMP can be affected there especially strongly. The carrier, preferably the insulating cover layer 1, may be designed locally or over its entire area such that it is optically active locally or over its entire area, e.g., due to the use of ZnO and $TiO_2$ as the material for the insulating cover layer 1. The biomaterial or biomolecule (e.g., viruses or bacteria) can also be destroyed in case of very strong activation of the carrier and the heat energy produced thereby. It is important for the optical activation that the photon or light energy be greater than the energy gap of the semiconductor material, of the ferroelectric or piezoelectric material or of the material of the insulating cover layer of the carrier.

The activation of the magnetizable charged imperfections in the carrier may analogously also be carried out by an external static magnetic field or a magnetic field varying over time and the heat energy thus produced can be passed on onto the biomaterial or biomolecules.

The insulating cover layer 1 on a semiconductor material may be omitted in case of the use of the optical activation of the carrier or in case of activation of the magnetizable charged imperfections in the carrier or in case of use under vacuum-like conditions. It is recommended in all other cases that an insulating cover layer 1 be applied to the semiconductor material.

It is recommended in case of ferroelectric or piezoelectric materials that an insulating cover layer 1 be applied in order to minimize interfering effects from the environment.

Figure 9:
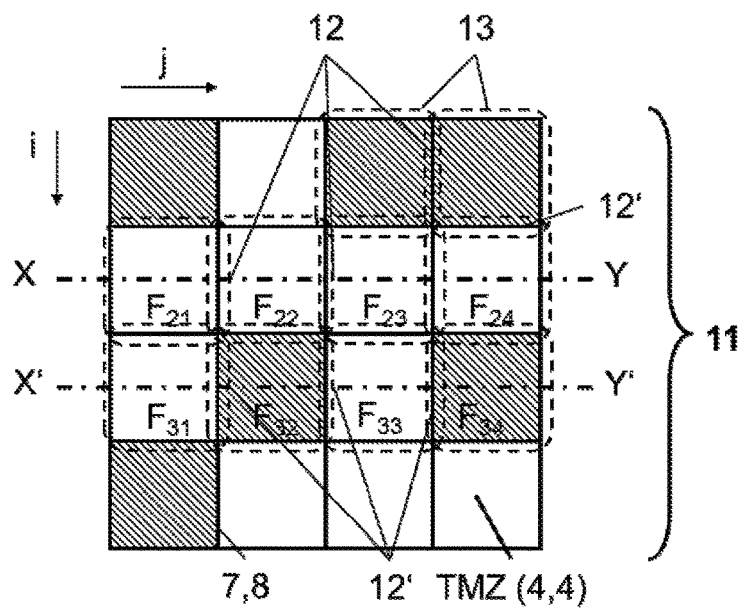
FIG. 9 is a view showing the gapless and overlapping-free classification of the carrier into uniform carrier cells TMZ (i,j)
Figure 10:
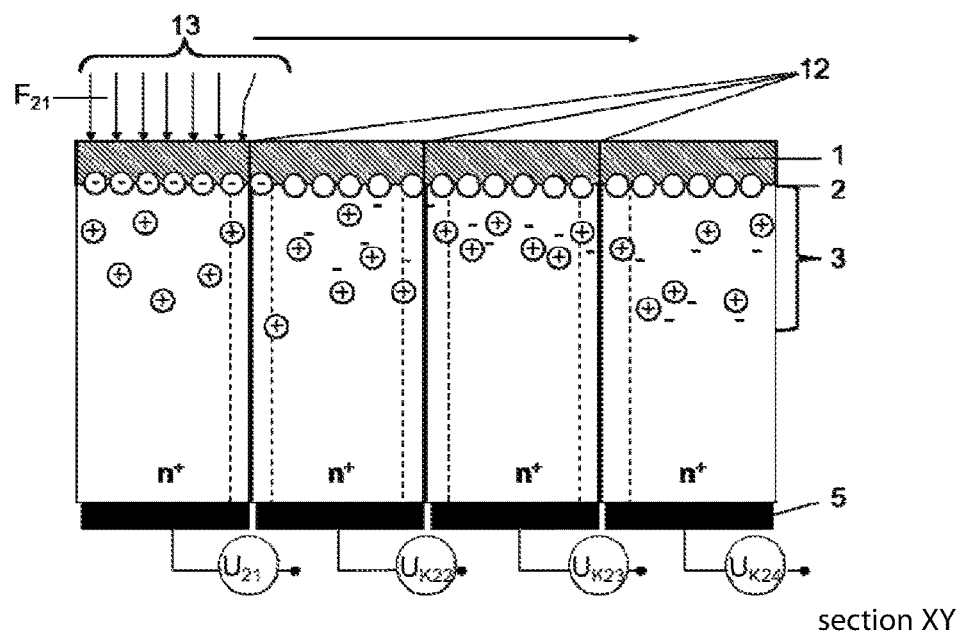
FIG. 10 is a view showing shows the section XY through four carrier cells of a semiconducting carrier with structured bottom electrode for translatory motions of epAIMP.

FIG. 9 shows the carrier 11 according to the present invention in an array structure with I rows and j columns in a top view. The carrier 11 is formed in a gapless and overlapping-free manner from individual carrier cells TMZ (i,j), e.g., square carrier cells. Each carrier cell comprises a semiconductor material or a piezoelectric or ferroelectric material, each optionally with insulating cover layer 1 and with a metallically conducting rear-side electrode.

The near-surface electrostatic forces $F_{ij}$ are determined by forming an asymmetric electrostatic dipole 3 in the semiconductor material or by polarization charges in the piezoelectric or ferroelectric material, by the thickness of the insulating cover layer 1 and by the voltage $U_{ij}$ applied to the metallically conducting rear-side electrode 5. Since electrostatic forces have a wide range, the range of action 13 of the electrostatic forces $F_{ij}$ is greater than the extension of the individual carrier cells TMZ(i,j). The overlapping area 12 of the near-surface electrostatic forces between adjacent carrier cells TMZ(i,j) of the array with identical direction of the electrostatic forces (FIG. 9) determines the translatory motion of the epAIM.

The section plane XY in Error! reference source not found characterizes carrier cells TMZ(2,1), TM (2,2), TM (2,3) and TM (2,4) adjoining each other with identical direction of the near-surface electrostatic forces $F_{21}$, $F_{22}$, $F_{23}$, $F_{24}$. The near-surface electrostatic forces $F_{22}$, $F_{23}$ and $F_{24}$ are reduced to zero in the figure by applying the corresponding Kelvin voltage $U_{K22}$, $U_{K23}$ and $U_{K24}$. Along the section plane XY, the superimposed near-surface electrostatic forces $F_{21}$, $F_{22}$, $F_{23}$, $F_{24}$ may have an especially great gradient by applying external, superimposed direct and alternating voltages $U_{21}$, $U_{22}$, $U_{23}$ and/or $U_{24}$ to the individual carrier cells TMZ(2,1), TMZ(2,2), TMZ(2,3) and TMZ(2,4) in the individual overlapping areas 12 between the individual carrier cells. This can be attributed to the fact that the gradient of the electrostatic forces $F_{21}$, $F_{22}$, $F_{23}$, $F_{24}$ with identical directions is homogeneous outside the overlapping areas 12 and can change its value continuously in the overlapping areas if the corresponding Kelvin voltage $U_{Kij}$ is applied on one or more adjacent carrier cells TMZ(i,j) to minimize the near-surface electrostatic force $F_{ij}$ and/or to reduce it to zero.

The dynamics of the translatory motion along the section plane XY is thus determined mainly by the overlapping areas 12.

Figure 11:
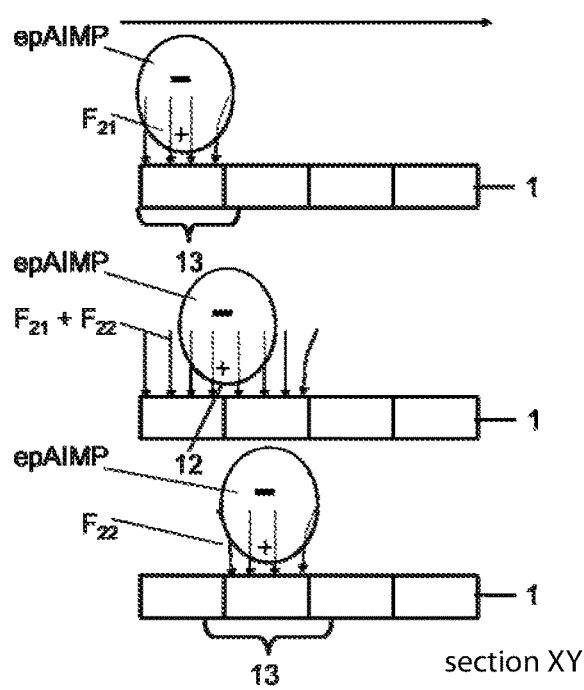
FIG. 11 is a schematic view showing the translation of an epAIMP based on the near-surface electrostatic forcesl.

FIG. 11 shows the translatory motion of an epAIMP M above the insulating layer 1 of the carrier cell along the section plane XY, whose forces have the same direction when an external voltage is applied. The force $F_{21}$ acts on the epAIMP M via the carrier cell TMZ(2,1) in the upper part of the figure. By changing the voltage $U_{22}$ applied to the carrier cell TMZ(2,2), the gradient of the electrostatic force $F_{21}+F_{22}$ is increased in the transition area 12 between TMZ(2,1) and TMZ(2,2) compared to force $F_{21}$ of TMZ(2,1), so that the epAIMP performs translatory motion to the overlapping area 12 (middle part of the figure). To conclude, the translatory motion shown from TMZ(2,1) to TMZ(2,2), the Kelvin voltage $U_{K12}$ is applied to TMZ(2,1), so that an electric force $F_{22}$ acts only via TMZ(2,2).

Figure 12:
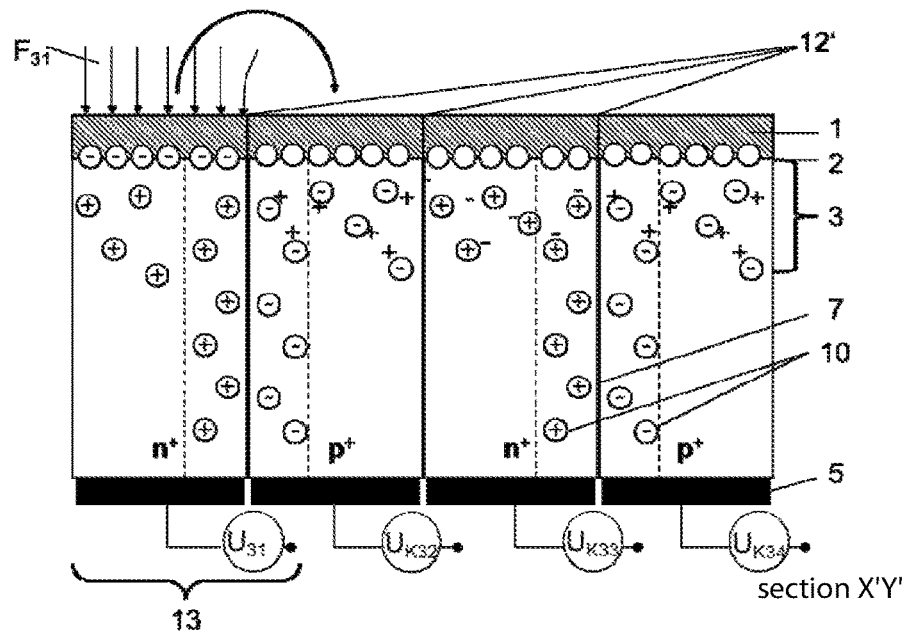
FIG. 12 is a sectional view X'Y' through four carrier cells of a semiconducting carrier with structured rear-side electrode for rotary motions.

The overlapping area 12' of the near-surface electrostatic forces between adjacent carrier cells TMZ(i,j) of the array with different directions of the electrostatic forces in FIG. 9 determines the rotatory motion of the epAIMP The section plane X'Y' in FIG. 12 characterizes carrier cells TMZ(3,1), TM (3,2), TM (3,3) and TM (3,4) adjoining each other with different directions of the near-surface electrostatic forces $F_{31}$, $F_{32}$, $F_{33}$, $F_{34}$. The near-surface electrostatic forces $F_{32}$, $F_{33}$ and $F_{34}$ are minimized in the figure by applying the corresponding Kelvin voltage $U_{K32}$, $U_{K33}$ and $U_{K34}$. These carrier cells are shown in a side view in FIG. 12. The gradient of the superposed near-surface electrostatic forces $F_{31}$, $F_{32}$, $F_{33}$, $F_{34}$ may be especially great in the overlapping areas 12' of the near-surface electrostatic forces of adjacent carrier cells along the section plane X'Y' due to application of an external voltage $U_{31}$, $U_{K32}$, $U_{K33}$ and $U_{K34}$ to the individual carrier cells TMZ(3,1), TM (3,2), TM (3,3) and TM (3,4). The dynamics of the rotatory motion along the section plane X'Y' is thus determined mainly by the overlapping areas 12'

Figure 13:
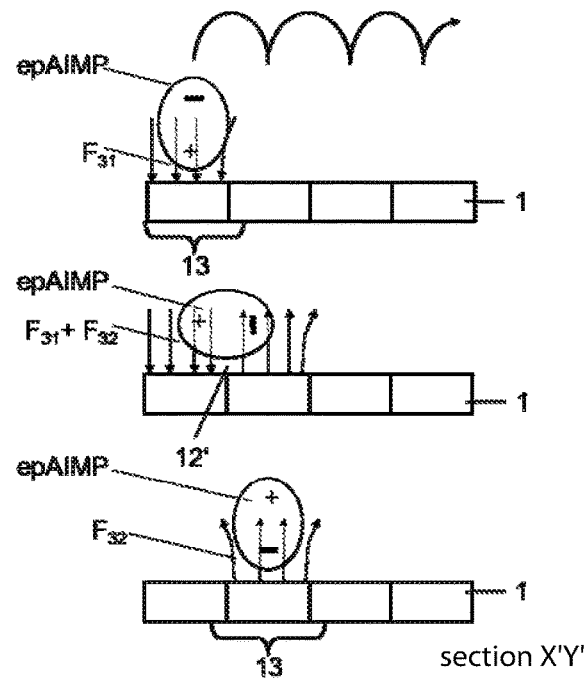
FIG. 13 is a schematic view showing the rotation of an epAIMP based on the near-surface electrostatic forces.

FIG. 13 schematically shows the rotation of an epAIMP based on the near-surface electrostatic forces.

Figure 14:
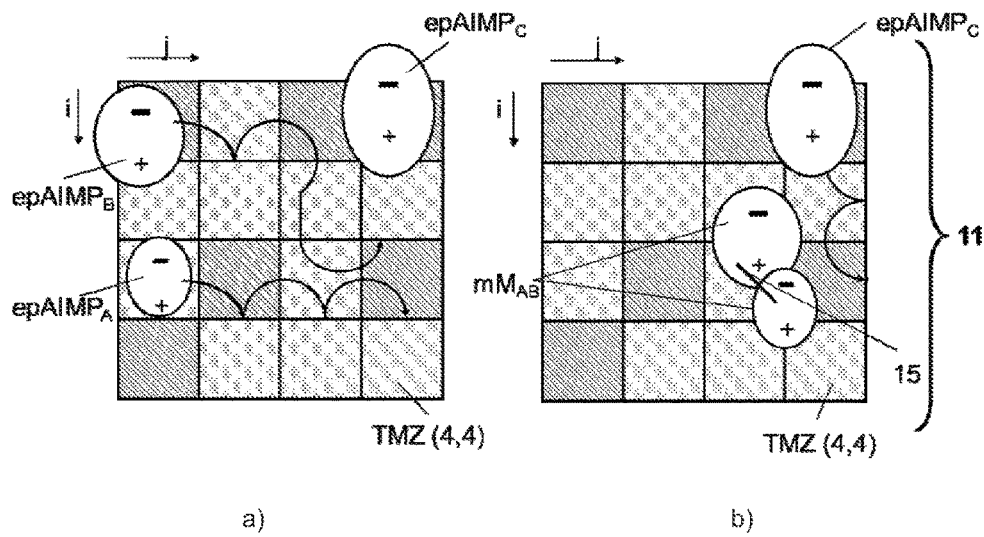
FIG. 14 is a view showing the successive assembly of a molecular machine from the components epAIMPA, epAIMPB and epAIMPC.
Figure 15:
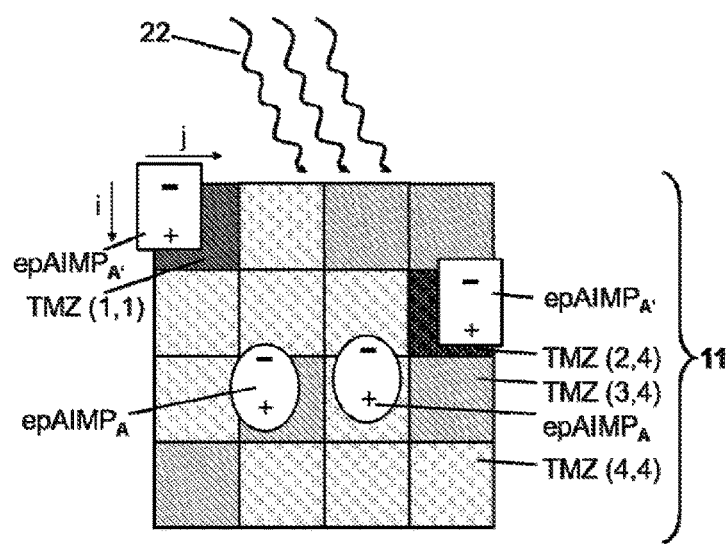
FIG. 15 is a view showing the electrically polarizable biomaterials, polyelectrolyte materials, atoms, ions and/or molecules (epAIMPA') in TMZ(1,1) and in TMZ(2,4), which are modified by electromagnetic waves 22.

FIG. 14 shows the carrier 11 according to the present invention in an array structure with I rows and j columns in a top view. The epAIMP $M_A$, $M_B$ and $M_C$ are localized on the carrier cells TMZ(3,1), TMZ(1,1) and TMZ (1,4) in FIG. 14 a). The epAIMP $M_A$ is moved rotatorily from TMZ(3,1) to TMZ(3,4) and epAIMP $M_B$ is moved rotatorily from TMZ (1,1) to TMZ (2,3), translatorily from TMZ (2,3) to TMZ (3,3), and rotatorily from TMZ(3,3) to TMZ(3,4). The two epAIMP $M_A$ and $M_B$ form a connection 15 (FIG. 14 b)). The epAIMP $M_C$ is then moved rotatorily from TMZ(1,4) to TMZ(3,4). The connected epAIMP $M_A$, $M_B$ and $M_C$ can form a molecular machine FIG. 15 shows the temperature-sensitive epAMIP$_A$ localized on TMZ(1,1) after the modification into epAIMP$_A$' and the temperature-sensitive epAIMP$_A$ localized on TMZ(2,4) after the modification to epAIMP$_A$'. The carrier cells TMZ (i,j) of the carrier 11 comprise semiconducting and/or piezoelectric or ferroelectric materials with different energy gaps $E_g$(i,j). As a result, light can be absorbed locally in TMZ(1,1) and in TMZ(2,4) and converted into heat energy in case of illuminating the carrier 11 over a large area with electromagnetic waves 22, preferably with light, from the rear side and/or from the front size of the carrier 11 with an energy lower than the energy gap of the carrier cells TMZ(3,2) and TMZ(3,3) and with an energy greater than the energy gap of the carrier cells TMZ(1,1) and TMZ(2,4)

Figure 16:
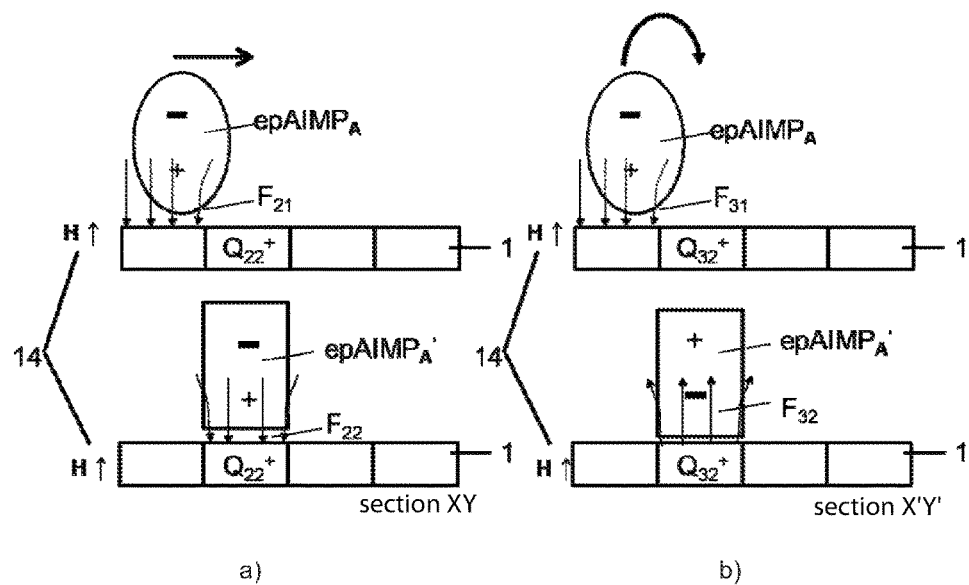
FIG. 16 is a view showing the electrically polarizable biomaterials, polyelectrolyte materials, atoms, ions and/or molecules (epAIMPA') in TMZ(2,2) and (epAIMPA') in TMZ(3,2), which are modified by a magnetic field H that is variable in time. The epAIMPA is moved by translatory (a) or rotatory (b) motion.

FIG. 16 a) shows the modification of the epAIMP$_A$ localized on TMZ(2,1) after a translatory motion from TMZ(2,1) to TMZ(2,2) along section XY in FIG. 11.

FIG. 16 b) shows the modification of the epAIMP$_A$ localized on TMZ(3,1) after a rotatory motion from TMZ (3,1) to TMZ(3,2) along section X'Y' in FIG. 13. The charged imperfections $Q^+$ introduced into the insulating cover layer 1 of TMZ(2,2) and TMZ(3,2) do not preferably affect the near-surface electrostatic forces $F_{22}$ (FIG. 16 a)) and $F_{32}$ (FIG. 16 b)) in this array and are magnetizable by a magnetic field H applied from the outside. If a magnetic field H that is variable over time is applied from the outside, the direction of magnetization of the imperfections $Q^+$ will change variably over time and heat energy is produced locally when the magnetization is reversed, which is used to modify temperature-sensitive epAIMP$_A$ on TMZ(2,2) and TMZ(3,2).

If the electrically polarizable biomaterials, polyelectrolyte materials, atoms, ions or molecules are additionally also magnetizable, the manipulation, modification and motion can then take place additionally due to near-surface magnetostatic forces, such as they occur, for example, in the vicinity of magnetizable imperfections $Q_M$.

Figure 17:
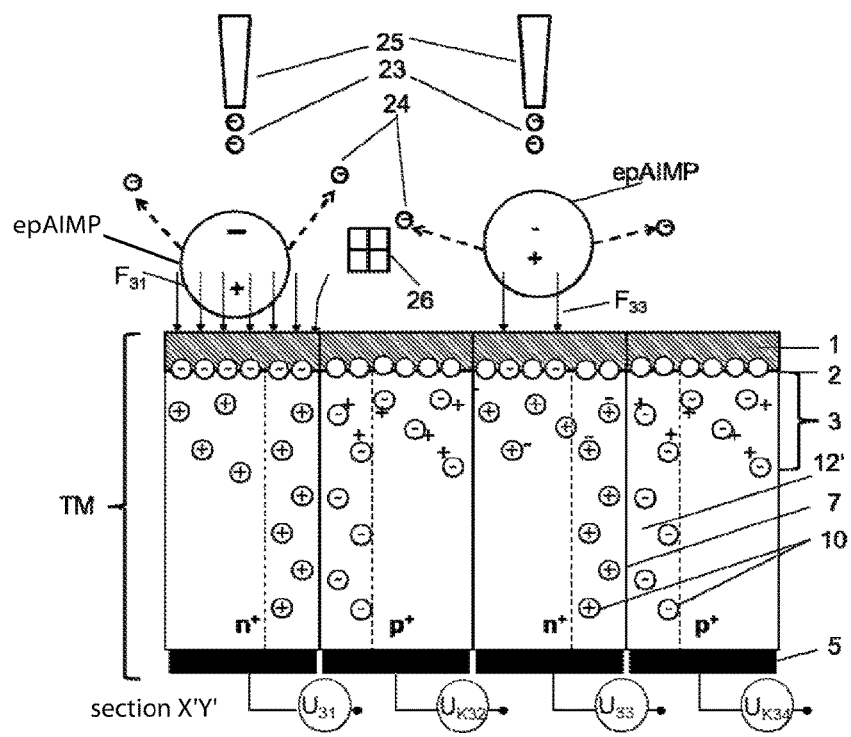
FIG. 17 is a view showing the marker-free, electric detection of electrically polarizable biomaterials, polyelectrolyte materials, atoms, ions and/or molecules (epAIMP) over the carrier TM by means of electron beams (23,24).

FIG. 17 shows the marker-free electric detection of electrically polarizable biomaterials, polyelectrolyte materials, atoms, ions and/or molecules (epAIMP) in powders, liquids, gases by means of primary electron beams (23) from at least one electron source (25), wherein the scattering of the secondary electrons (24), which are formed by the impingement of the primary electrons (23) on epAIMPs, depends on the electric polarization of the epAIMP and is determined by means of an electron detector (26), wherein the scattering of the secondary electrons is set by the electric polarization of the epAIMP by means of changing the near-surface electrostatic forces on the carrier TM, utilizing the manipulation, modification and translatory and rotatory motion of the epAIMP.

While specific embodiments of the invention have been shown and described in detail to illustrate the application of the principles of the invention, it will be understood that the invention may be embodied otherwise without departing from such principles.

The invention claimed is:

1. A carrier for the modification, manipulation and motion of electrically polarized or polarizable biomaterials, polyelectrolyte materials, atoms, ions and/or molecules (epAIMP), the carrier comprising:
   semiconducting or piezoelectric material;
   an electrically insulating coating layer on the surface of the semiconducting or piezoelectric material, wherein electrostatic forces act on the epAIMP through the electrically insulating coating layer, wherein the electrostatic forces are generated and their force is determined by one of:
   an asymmetric electrostatic dipole developing on a basis of an occupation of interface states between the semiconducting material and the electrically insulating coating layer, wherein an interface state density in the boundary layer between the electrically insulating coating layer and the semiconductor material varies in the range of $10^7$ cm$^{-2}$ eV$^{-1}$ to $10^{14}$ cm$^{-2}$ eV$^{-1}$, and a time constant of the interface states in the boundary layer between the electrically insulating coating layer and the semiconductor material is in the range of a few nanoseconds to seconds, as well as a near-surface doping of the semiconducting material; and a number of near-surface polarization charges and a thickness of the piezoelectric material, and wherein a force of the electrostatic forces is determined by a type and a thickness of the material of the electrically insulating coating layer, wherein at least one metallically conducting rear-side electrode is arranged on a side of the carrier located opposite to the electrically insulating coating layer.

2. A carrier in accordance with claim 1, wherein the thickness of the electrically insulating coating layer is less than 20 nm.

3. A carrier in accordance with claim 2, wherein the electrically insulating coating layer comprises an upper surface and a lower surface, the lower surface being in direct contact with the semiconducting or piezoelectric material, the thickness being defined exclusively by the upper surface and the lower surface.

4. A carrier in accordance with claim 1, wherein the at least one metallically conducting rear-side electrode is located at a spaced location from the electrically insulating coating layer.

5. A carrier in accordance with claim 4, wherein the rear-side electrode is structured in a strip-shaped pattern.

6. A carrier in accordance with claim 1, wherein:
the carrier is arranged as an array structure;
the carrier has individual carrier cells, which are formed flatly by different polygons; and
corner points of the polygons are connected with one another in a straight and/or curved manner in pairs.

7. A carrier in accordance with claim 6, wherein each carrier cell or individual carrier cells is/are each provided with a metallically conducting rear-side electrode of its/their own.

8. A carrier in accordance with claim 6, further comprising magnetizable imperfections introduced in individual carrier cells, in the electrically insulating coating layer or in a near-surface region of the semiconducting or piezoelectric materials.

9. A carrier in accordance with claim 1, wherein magnetizable imperfections are introduced in the carrier material, in the electrically insulating coating layer or in the near-surface region of the semiconducting or piezoelectric materials.

10. A carrier in accordance with claim 1, wherein:
the carrier comprises a semiconductor material; and
individual charged impurities are introduced locally into the semiconductor material and/or locally into the electrically insulating coating layer in order to affect near-surface electrostatic forces.

11. A carrier in accordance with claim 1, wherein:
the carrier comprises a piezoelectric material; and
the piezoelectric material and/or the electrically insulating coating layer comprises charged impurities.

12. A carrier in accordance with claim 1, wherein at least one transition region is formed between two adjacent regions with respective reversed directions of the near-surface electrostatic forces in the carrier by applying a voltage to one or more rear-side electrodes of the carrier for the manipulation, modification and motion of electrically polarizable biomaterials, polyelectrolyte materials, atoms, ions and/or molecules (epAIMP) variable in time and space.

13. A carrier in accordance with claim 1, wherein the thickness of the electrically insulating coating layer is less than 5 nm.

14. A carrier in accordance with claim 1, wherein the thickness of the electrically insulating coating layer is between 2 nm and 3 nm.

15. A carrier in accordance with claim 1, wherein an interface state density in the boundary layer between the electrically insulating coating layer and the semiconductor material varies in the range of $10^{12}$ cm$^{-2}$eV$^{-1}$ to $10^{14}$ cm$^{-2}$eV$^{-1}$, and the time constant of the interface states in the boundary layer between the electrically insulating coating layer and the semiconductor material is in the range of nanoseconds to about 10 milliseconds.

16. A carrier in accordance with claim 1, wherein a dynamic change of the electrostatic forces is generated by only one rear-side electrode, the one rear-side electrode being arranged on a side of the carrier located opposite to the electrically insulating coating layer.

17. A carrier for the modification, manipulation and motion of electrically polarized or polarizable biomaterials, polyelectrolyte materials, atoms, ions and/or molecules (epAIMP), the carrier comprising:
semiconducting or piezoelectric material;
an electrically insulating coating layer on the surface of the semiconducting or piezoelectric material; the semiconducting or piezoelectric material and the electrically insulating coating layer comprising interface states, wherein an asymmetric electrostatic dipole is formed based on the interface states between the electrically insulating coating layer and the semiconducting or piezoelectric material, wherein an interface state density in a boundary layer between the electrically insulating coating layer and the semiconducting or piezoelectric material varies in a range of $10^7$ cm$^{-2}$ eV$^{-1}$ to $10^{14}$ cm$^{-2}$ eV$^{-1}$, and a time constant of the interface states in the boundary layer between the electrically insulating coating layer and the semiconducting or piezoelectric material is in a range of a few nanoseconds to seconds, wherein electrostatic forces act on the epAIMP through the electrically insulating coating layer, wherein a force of the electrostatic forces is based on at least the asymmetric electrostatic dipole, wherein at least one metallically conducting rear-side electrode is arranged on a side opposite the electrically insulating coating layer.

18. A carrier in accordance with claim 17, wherein the at least one metallically conducting rear-side electrode is located at a spaced location from the electrically insulating coating layer.

19. A carrier for the modification, manipulation and motion of electrically polarized or polarizable biomaterials, polyelectrolyte materials, atoms, ions and/or molecules (epAIMP), the carrier comprising:
semiconducting or piezoelectric material;
an electrically insulating coating layer on the surface of the semiconducting or piezoelectric material;
a boundary layer between the semiconducting or piezoelectric material, the boundary layer comprising interface states, wherein an asymmetric electrostatic dipole is provided between the semiconducting or piezoelectric material and the electrically insulating coating layer based on the interface states, wherein an interface state density in the boundary layer between the electrically insulating coating layer and the semiconductor material varies in a range of $10^7$ cm$^{-2}$ eV$^{-1}$ to $10^{14}$ cm$^{-2}$ eV$^{-1}$, and a time constant of the interface states in the boundary layer between the electrically insulating coating layer and the semiconductor material is in the range of a few nanoseconds to seconds, at least the asymmetric dipole generating electrostatic forces, the electrostatic forces acting on the epAIMP through the electrically insulating coating layer, wherein a magnitude of the electrostatic forces is based on at least the asymmetric electrostatic dipole;

a metallically conducting rear-side electrode arranged on a side of the carrier located opposite the electrically insulating coating layer.

20. A carrier in accordance with claim 19, wherein another metallically conducting rear-side electrode is located at a spaced location from the electrically insulating coating layer to provide a plurality of rear-side electrodes of carrier cells, wherein the rear-side electrodes of the carrier cells are separated from each other.

\* \* \* \* \*